US009057803B2

(12) United States Patent
Christian et al.

(10) Patent No.: US 9,057,803 B2
(45) Date of Patent: *Jun. 16, 2015

(54) METHODS, APPARATUS AND SYSTEMS FOR MEASURING SNOW STRUCTURE AND STABILITY

(71) Applicant: AvaTech, Inc., Cambridge, MA (US)

(72) Inventors: James Loren Christian, Cambridge, MA (US); Samuel Tileston Whittemore, Readfield, ME (US); Brinton Johnston Wadsworth Markle, Cambridge, MA (US)

(73) Assignee: AVATECH, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/063,649

(22) Filed: Oct. 25, 2013

(65) Prior Publication Data

US 2014/0116127 A1  May 1, 2014

Related U.S. Application Data

(60) Provisional application No. 61/718,471, filed on Oct. 25, 2012, provisional application No. 61/822,284, filed on May 10, 2013.

(51) Int. Cl.
*G01W 1/00* (2006.01)
*G01W 1/14* (2006.01)
(Continued)

(52) U.S. Cl.
CPC ............. *G01W 1/14* (2013.01); *G01B 21/18* (2013.01); *G01N 3/00* (2013.01); *G01N 17/00* (2013.01);
(Continued)

(58) Field of Classification Search
None
See application file for complete search history.

(56) References Cited

U.S. PATENT DOCUMENTS 3,988,923 A   11/1976   Elmiger et al.
4,820,051 A    4/1989   Yanagisawa et al.
(Continued)

FOREIGN PATENT DOCUMENTS

EP    0760989 A1    3/1997
EP    1202078 A2    5/2002
(Continued)

OTHER PUBLICATIONS

Schneebeli, M. et al., "Measuring Snow Microstructure and Hardness Using a High Resolution Penetrometer," Cold Regions Science and Technology, vol. 30, No. 1-3, pp. 305-311 (1999).
(Continued)

*Primary Examiner* — Andre Allen
(74) *Attorney, Agent, or Firm* — Wilmer Cutler Pickering Hale and Dorr LLP

(57) ABSTRACT

The present inventions relate generally to methods, apparatus and systems for measuring snow stability and structure which may be used to assess avalanche risk. The disclosed apparatus includes a sensing unit configured to measure a size of snow grains as the sensing unit is being driven into a layer of snow. The disclosed apparatus may also be configured to take other environmental measurements, including resistance to penetration, temperature, humidity, slope aspect and inclination. Methods and apparatus are also disclosed for generating a profile of snow grain size according to depth based on the measured size of snow grains. Systems and apparatus are also disclosed for sharing the generated profiles among a plurality of users via a central server, and for evaluating an avalanche risk at a geographic location.

17 Claims, 25 Drawing Sheets

(51) Int. Cl.
  *G01B 21/18* (2006.01)
  *G01N 3/00* (2006.01)
  *G01N 17/00* (2006.01)
  *G01B 7/26* (2006.01)
  *G08C 17/02* (2006.01)
  *G01N 3/42* (2006.01)

(52) U.S. Cl.
  CPC *G01B 7/26* (2013.01); *G08C 17/02* (2013.01); *G01N 3/42* (2013.01); *G01N 2203/0082* (2013.01)

(56) References Cited

U.S. PATENT DOCUMENTS

| | | | |
|---|---|---|---|
| 5,661,464 | A | 8/1997 | Bilak et al. |
| 5,831,161 | A | 11/1998 | Johnson et al. |
| 6,313,645 | B1 | 11/2001 | Brandelik et al. |
| 6,351,988 | B1 | 3/2002 | Bartlett |
| 6,957,593 | B1* | 10/2005 | Burns .................. 73/866 |
| 7,040,146 | B2* | 5/2006 | Mackenzie et al. ........ 73/81 |
| 7,564,477 | B2 | 7/2009 | Kirby |
| 7,628,059 | B1 | 12/2009 | Scherbring |
| 2005/0076709 | A1* | 4/2005 | Mackenzie et al. ........ 73/81 |
| 2006/0171579 | A1 | 8/2006 | Lee et al. |
| 2008/0198027 | A1 | 8/2008 | Bugge |
| 2010/0148946 | A1 | 6/2010 | Strombeck et al. |
| 2011/0226044 | A1 | 9/2011 | Hughes et al. |
| 2012/0004848 | A1 | 1/2012 | Kinast et al. |
| 2012/0242488 | A1 | 9/2012 | Wilson |
| 2014/0116157 | A1* | 5/2014 | Christian et al. ...... 73/862.627 |
| 2014/0116162 | A1* | 5/2014 | Christian et al. ............ 73/866 |
| 2014/0118165 | A1* | 5/2014 | Christian et al. ...... 340/870.07 |

FOREIGN PATENT DOCUMENTS

| | | |
|---|---|---|
| EP | 2444132 A1 | 4/2012 |
| WO | WO-03056302 A1 | 7/2003 |

OTHER PUBLICATIONS

Mackenzie, R and Payten, W., A Portable, Variable-Speed, Penetrometer for Snow Pit Evaluation; Mountain Snowpack, International Snow Science Workshop (2002: Penticton, B.C.) 294-300.

Floyer, J.A. and Jamieson, J.B., Rate-effect experiments on round-tipped penetrometer insertion into uniform snow. J Glaciol 56(198):664-672, 2010.

Floyer, J. and Jamieson, B., Avalanche Weak Layer Tracing and Detection in Snow Penetrometer Profiles. Proceedings of the 4th Canadian Conference on Geohazards:From Causes to Management. Presse de l'Université Laval, Québec, 594 p. (2008), 8 pages.

* cited by examiner

METHODS, APPARATUS AND SYSTEMS FOR MEASURING SNOW STRUCTURE AND STABILITY

This application claims the benefit of priority to U.S. Provisional Application Nos. 61/718,471 filed Oct. 25, 2012 and 61/822,284 filed May 10, 2013, both of which are hereby incorporated by reference in their entirety.

TECHNICAL FIELD

The present disclosure relates to a portable device for assessing the structure and stability of a layer of snow.

BACKGROUND

Every year, hundreds of people around the world die in avalanches because they lack crucial information about the stability of the snowpack. Annual avalanche fatalities have increased by 220% over the past two decades, fueled by a rapidly growing interest in backcountry sports, now the fastest growing segment of the snow sports industry. Moreover, avalanche risk is not limited to recreationalists, but affects the military, researchers, search and rescue personnel, transportation authorities, and alpine mining operations alike.

Current approaches to avalanche safety are reactive. Beacons, probes, shovels, and avalanche airbags are all designed to help increase chances of survival after you've been trapped in an avalanche. With a fatality rate greater than 50% for those buried in an avalanche, these devices fail to address the real need—avoiding avalanches altogether. Today's manual snow pit methods to detect weak layers in the snow under foot are highly error prone, time-consuming, subjective, and only provide information about conditions in one location. There is a significant need for a low-cost device that can increase the speed and accuracy with which snowpack profiles can be evaluated.

SUMMARY OF THE DISCLOSURE

In one aspect, the present disclosure is directed at an apparatus for measuring snow structure and stability. The apparatus can include a pole having a length, a first end and a second end; a sensing unit located at the first end of the pole, the sensing unit including a head shaped for probing a layer of snow, the sensing unit configured to measure a size of snow grains within the layer of snow; and a range sensor configured to measure a distance between the range sensor and a surface of the layer of snow. The apparatus can also include a processor configured to determine a depth of penetration based on the distance measured by the range sensor and the length of the pole; and determine a profile of snow grain size according to depth based on the measured size of snow grains measured by the sensing unit.

In some embodiments, the sensing unit of the apparatus can include a camera configured to record images of the layer of snow.

In some embodiments, the apparatus of the present disclosure can include a data display screen configured to display the recorded images of the layer of snow.

In some embodiments, the sensing unit of the apparatus can include a snowpack resistance sensor configured to measure a resistance to penetration of the layer of snow.

In some embodiments, the sensing unit of the apparatus can measure the size of snow grains based on changes in the measured resistance to penetration resulting from the loading and rupturing of individual bonds between snow grains.

In some embodiments, the sensing unit of the apparatus can include a tip cylinder, a resistance sensing element disposed within the tip cylinder, and a weather-sealing filler which fills a space between the resistance sensing element and the tip cylinder, wherein the weather-sealing filler is configured to deform to allow the resistance sensing element to displace.

In some embodiments, the apparatus can include an optical sensor configured to measure a distance of displacement, and wherein the processor is configured to determine the depth of penetration based at least in part on the distance of displacement measured by the optical sensor.

In some embodiments, the apparatus can include an accelerometer, wherein the processor is configured to determine the depth of penetration based at least in part on an acceleration measured by the accelerometer.

In some embodiments, the apparatus can include a data display screen.

In some embodiments, the apparatus can include a wireless communication device configured to automatically determine the geographical position of the apparatus.

In some embodiments, the apparatus can include a wireless communication module for communicating with at least one of a wireless data network and a mobile device.

In some embodiments, the range sensor of the apparatus can be configured to measure distance by transmitting and receiving a beam of radiation.

In some embodiments, the range sensor of the apparatus can be configured to measure distance using sound waves.

In another aspect, the present disclosure is directed at a method for measuring snow structure and stability which can include: (a) measuring, at a probe that is being inserted progressively deeper into a snow layer, a size of snow grains within the snow layer; (b) measuring a depth of penetration based on the distance measured by a range sensor; and (c) repeating steps (a)-(b) to determine a profile of snow grain size according to depth based on the measured size of snow grains and the measured depth of penetration.

In some embodiments, the method can include determining to start a test based on at least one of a sensed resistance to penetration and input from an optical sensor; and determining to end the test when the measured depth of penetration decreases or remains constant for a predetermined period of time.

In some embodiments, the method can include averaging the measured sizes of snow grains that are within a predetermined threshold of each other.

In some embodiments, the method can include measuring the depth of penetration based at least in part on a displacement measured by an optical sensor.

DESCRIPTION

Figure 1:
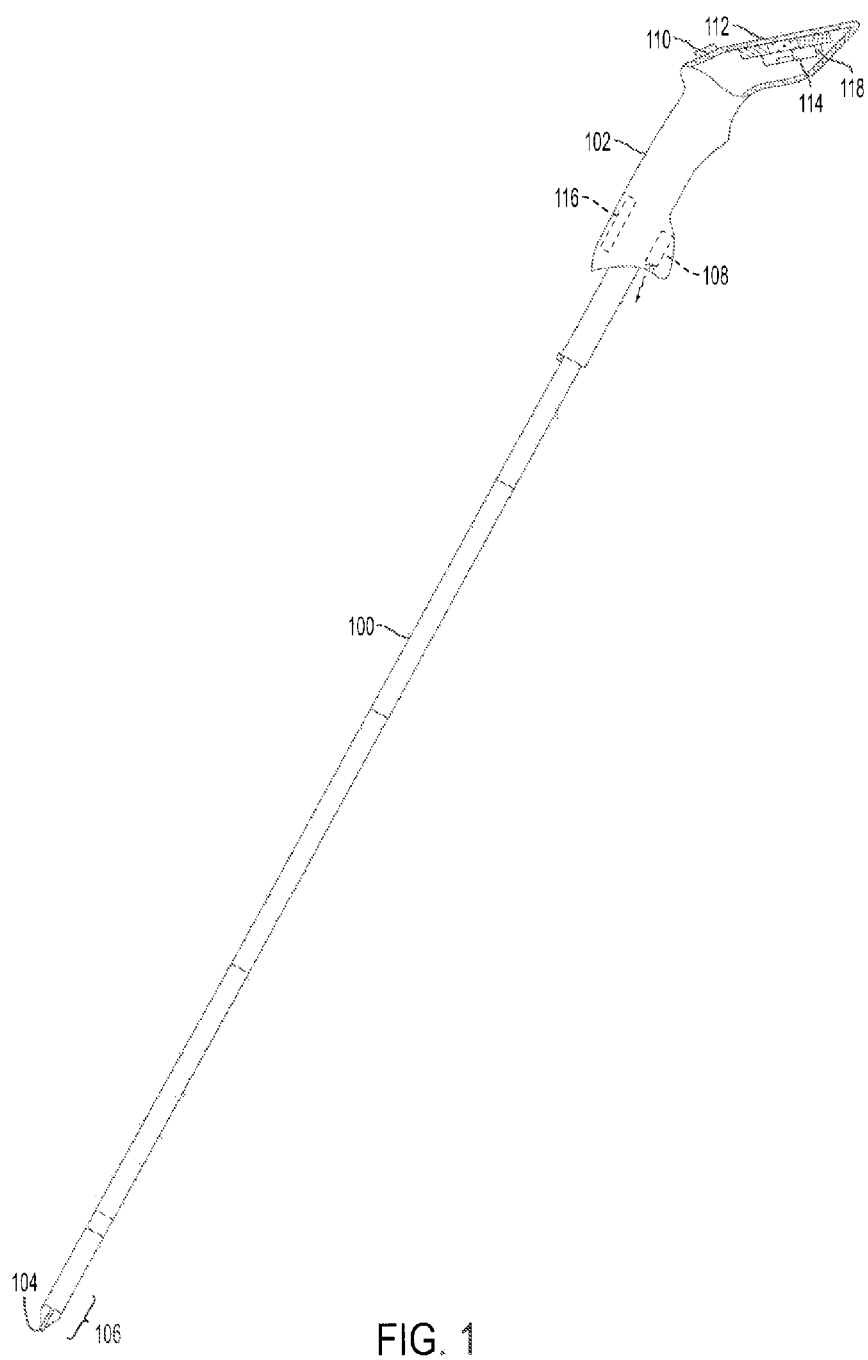
FIG. 1 is a diagram of an example snow-measurement device in its extended position, according to embodiments of the present disclosure.

The system can introduce a portable handheld snowpack measurement tool (the "snow-measurement device" or "device") that helps users more quickly and accurately assess snowpack and other avalanche risk factors, helping them make informed travel decisions in avalanche terrain. The device can also be used for purposes unrelated to avalanches, such as hydrology and soil measurement, among others. Additionally, the system includes a way of sharing user and geographic specific information with other users via an online database. The physical device measures and saves snowpack information, which the user can then upload to the database for other users' benefit. In this way, the physical device crowd sources safety information across a broad network of users and integrates and tracks this data over time online. Finally, the system includes a data interpretation component, where aggregated data is analyzed to look for trends between individual data results and large-scale avalanche activity and changes in snow structure.

An example of a consumer use scenario for this product would be a backcountry skier who takes periodic measurements with the device while traveling up a mountain in avalanche terrain. The measurements she acquires on her journey up the mountain helps her understand the features of the snowpack, and inform her decision about where she feels it is safe or unsafe to travel in the terrain. The user is able to share information across device user interfaces, extract valuable data from external sources, and report localized conditions externally. With many datasets in the database, trends relating snow structure, location, terrain characteristics, avalanche risk, water resources, and weather patterns can be uncovered.

An example of a professional use scenario for this product would be a mountain guide, avalanche forecaster, ski patroller, or scientist that takes frequent measurements with the device while in mountain terrain to better ensure the safety of their clients resort, or for scientific and snow study purposes. With the ability to gather more information in real-time, view information from across the network, and track this information historically, avalanche professionals can not only be able to make better terrain management decisions, they can also be able to make better forecasts. In a similar manner, hydrologists and snow scientists can be able to use this tool to gather stratigraphic and micro-structural snow data, and ultimately draw better conclusions about snow and water resources around the globe. Additionally, the oil sands industry can benefit from this apparatus by being able to quickly evaluate the hardness of surface oil layers to determine the sands' readiness for collection and further processing.

In one embodiment, the device can be a portable or hand held tool that allows the user to assess snowpack risks in real time while traveling in snowy terrain.

The device can use a snow penetration resistance sensor and a depth sensor for determining the depth of the snow penetration resistance sensor. The device also can include other subsystems necessary for recording and displaying how the snowpack's resistance to penetration varies with depth. This knowledge can contribute to identifying areas with avalanche potential.

Combined with additional sensor readings, such as, but not limited to, slope inclination, slope orientation, ambient temperature, temperature profile of a snow layer as a function of depth, snow grain size, snow grain size profile as a function of depth, wind, weather forecast, weather history, user weight, altitude, snow water content, layer energy, and geolocation, the device can give users a quick, easy-to-read data output of the snow features with unprecedented accuracy and ease of use, thereby improving backcountry information management and potentially safety.

FIG. 1 is a schematic view of an exemplary device in the extended position, according to some aspects of the present disclosure. In some embodiments, the device can include a one-meter or longer collapsible cylindrical pole 100 with a handle 102 on one end, and a snowpack resistance sensor 104 on the other end. Pole 100 can be made of aluminum, steel, titanium, carbon fiber, plastic, and/or other materials that can be made into tubing. Handle 102 can be made of rubber, metal, and/or plastic, or any other moldable, machinable, or otherwise formable material. Other snowpack measurement sensors (i.e. temperature) can also be incorporated into a tip 106 (tip 106 refers to the end of the probe and any snowpack measurement sensors located there, and snowpack resistance sensor 104 is said to be part of tip 106). One or more sensors for determining the depth of tip 106 can be incorporated into the device (e.g., snow depth sensor 108 (see FIG. 2A), optical flow sensor 208 (see FIG. 2B)). Handle 102 serves as a place for the user to grab the device with their hand(s) and push the pole 100 through the snow to obtain a measurement. Additionally, handle 102 can contain embedded electronics, including, but not limited to: user interface buttons 110, a display 112, an accelerometer 118, and an electronic circuit 114 necessary for collecting, processing, displaying, and transmitting data and snowpack measurements. Finally, a power supply 116 is embedded in the handle and provides power to electronic circuit 114 and snowpack measurement sensors 104 and snow depth sensor 108, as well as any other sensors located in the device.

The device can optionally be equipped with a ski pole basket (not shown) at tip 106 to double as a ski or hiking pole. In this case, a cover can slide over tip 106 to prevent it from damage. Additionally, a collapsible extension can be added at tip 106 to increase the overall length so that the device can be used as an avalanche rescue probe in emergency situations.

Figure 2A:
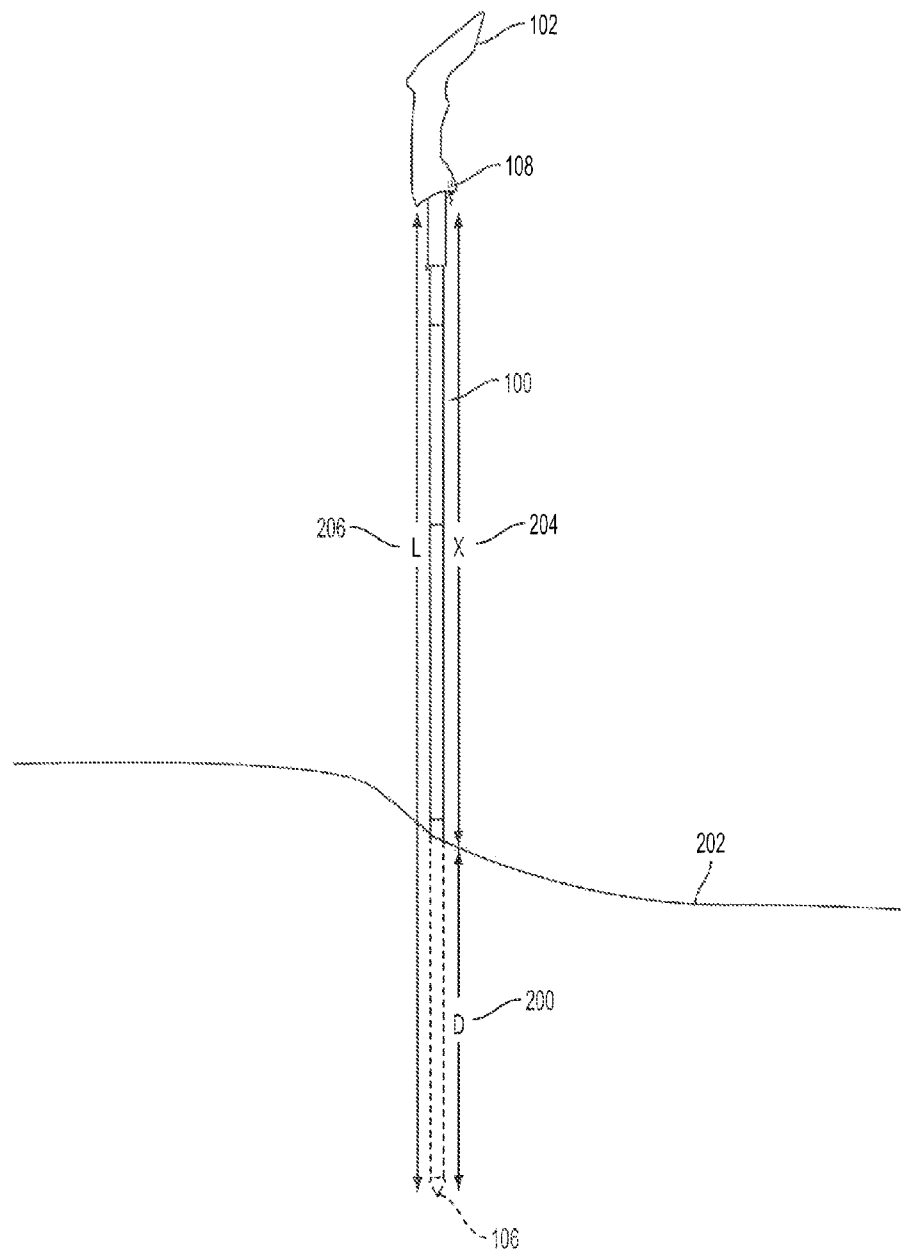
FIG. 2A is an illustration of how an example snow-measurement device measures the depth of its tip beneath a snowpack using a range sensor, according to embodiments of the present disclosure.

FIG. 2A is a schematic illustration of how snow depth sensor 108 operates to measure the depth of tip 106, according to some aspects of the present disclosure. The depth 200 of tip 106 is measured as the probe penetrates a snowpack 202. This is done by range-finding snow depth sensor 108, which calculates the depth 200 (D) of the tip 106 by subtracting a distance 204 (X) to the snow surface from a pre-determined probe length 206 (L). Range-finding snow depth sensor 108 may comprise an infra-red (IR) range-finding device, a radio frequency (RF) range-finding device, or a range-finding device that operates by sending and receiving sound- or pressure-waves (e.g., an ultrasonic range sensor).

The pole diameter can be ¾ inches or less so that less force is required to push the probe through the snowpack. As device tip 106 enters snow layers of different hardness, a different amount of force is required to penetrate the different hardness layers. However, the variations in force required to penetrate the snowpack is reduced by choosing a small diameter pole, which can result in a penetration closer to constant speed. Because penetration resistance is somewhat dependent on penetration speed, better data can be recorded with a smaller diameter pole where penetration speed is near constant. If penetration resistance is dependent on speed, a lookup table can be used to adjust measured resistance based on the speed at which that resistance was measured. A lookup table for speed correction can be used because the speed of penetration can be calculated at any given point based on the rate of change of the depth 200. The average speed between two depth readings taken close together can show a speed very close to tip's 106 actual speed through snowpack 202.

Figure 2B:
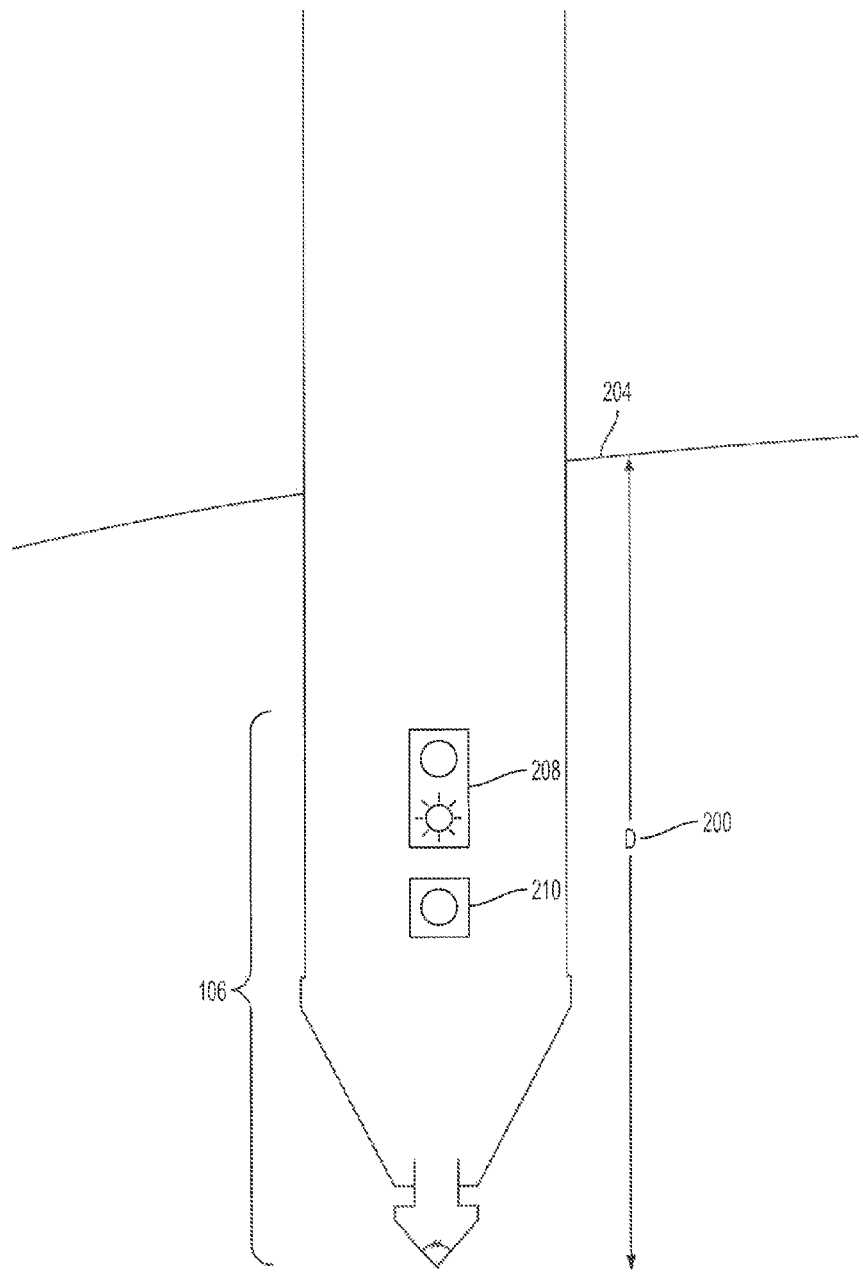
FIG. 2B is a diagram of the tip of an example snow-measurement device incorporating an optional optical flow sensor and optical trigger, according to embodiments of the present disclosure.

FIG. 2B shows an alternative embodiment, where depth 200 of tip 106 is calculated using an optical flow sensor 208 (such as those found in any optical computer mouse) on tip 106, according to some aspects of the present disclosure. Here, optical flow sensor 208 is mounted at tip 106 and oriented to look radially outward into snowpack 202. This is possible because tip 106 slides through snowpack 202, and optical flow sensor 208 can derive displacement based on the changing image it sees as it slides by the snow.

Additionally, an optical trigger 210 can be incorporated into tip 106 to detect the exact moment when tip 106 enters the snowpack 202. If the optical flow sensor 208 is not incorporated, optical trigger 210 is useful for providing the device with an absolute reference for the beginning of the test. Optical trigger 210 may be a photoresistor.

Another embodiment uses both range-finding snow depth sensor 108 and optical flow sensor 208. This is advantageous over using a single sensor because range-finding sensors suitable for snow depth sensor 108 show absolute depth with some error, and optical flow sensor 208 shows relative motion with some error. If necessary, more accurate movement of the device can be measured by having both an absolute depth sensor (such as snow depth sensor 108) and a relative motion sensor (such as optical flow sensor 208). Combining these technologies may also be useful if one sensor has a limited sample rate, because the other sensor can then be used to fill in information between samples taken at a limited rate.

Ultimately, incorporation of the above sensors can provide a depth measurement at a time interval dependent on the maximum sample rate of said depth measurement sensors. Infrared and ultrasonic sensors typically have sampling rates lower than snowpack resistance sensor 104, requiring that depth values between depth measurement sensor readings be determined by interpolation. While linear interpolation is a good approximation if speed is near constant between depth measurement sensor readings, better results can be obtained if the interpolation incorporates data from accelerometer 118 to account for speed changes between depth measurements. While accelerometer 118 is shown mounted in handle 102 in FIG. 1, it is to be understood that the accelerometer may be mounted anywhere in the device, including pole 100 or tip 106. Similarly, optical flow sensor 208 can provide information about these speed changes.

Figure 3A:
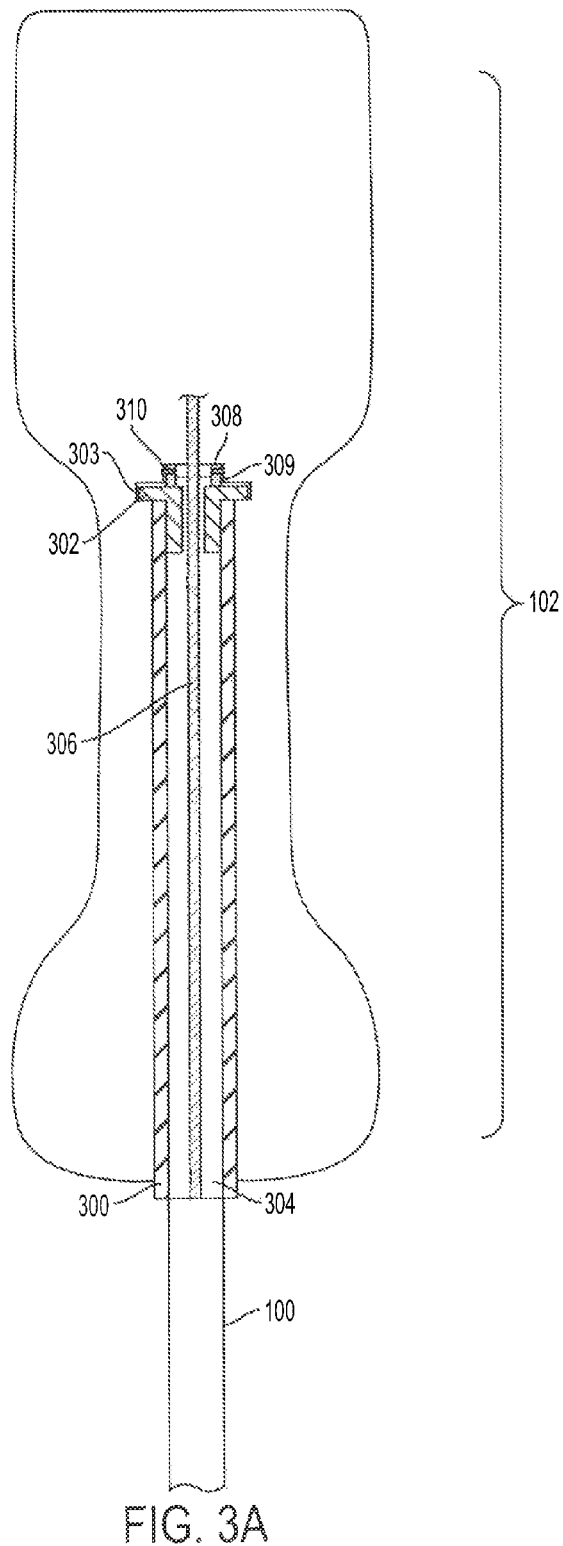
FIG. 3A is a diagram depicting a cross-section view of the connection between an example snow-measurement device's handle and pole, according to embodiments of the present disclosure.

FIG. 3A is a schematic cross-section view illustrating how handle 102 can connect to the top of cylindrical pole 100, according to some aspects of the present disclosure. Drawn is one half of handle 102. Handle 102 fits around cylindrical sliding tube 300. A flanged stop 302 is press fit, glued, or welded into the sliding tube 300, and the flange sits inside a flange groove 303 in handle 102 to prevent sliding tube 300 from sliding along its axis inside handle 102. A cylindrical upper pole segment 304 fits inside sliding tube 300 to form a sliding fit. A multi-conductor tether 306 runs inside a hole through the axis of flanged stop 302. An upper tether collar 308 is fixed onto the tether 306 with tether collar set screws 310, preventing tether 306 from sliding inside upper tether collar 308. Upper tether collar 308 sits inside a collar groove 309 in handle 102, which anchors both upper tether collar 308 and tether 306 in handle 102.

Figure 3B:
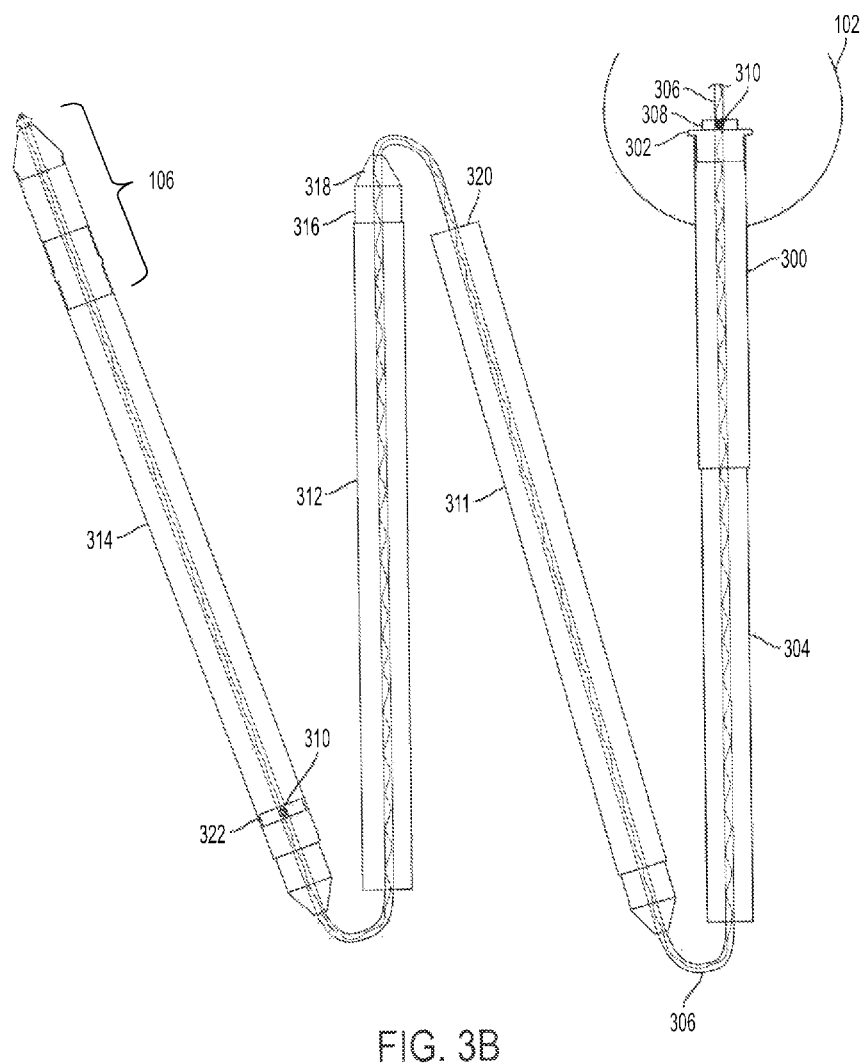
FIG. 3B is a diagram depicting the segments which comprise an example snow-measurement device's pole, according to embodiments of the present disclosure.

FIG. 3B is a schematic illustration showing the collapsed device folded into approximately one quarter of the full, extended length, according to some aspects of the present disclosure. Continuing away from handle 102 (see above, FIG. 3A) and towards tip 106, tether 306 runs through upper pole segment 304, and then through an upper-mid pole segment 311, a lower-mid pole segment 312, and a lower pole segment 314. The tether terminates at tip 106, where it is electrically connected to any snowpack measurement sensors in the tip 106, creating an electrical and mechanical connection between handle 102 and tip 106. At interfaces between pole segments there is a ferrule 316 and a ferrule cone 318 on one pole segment and a ferrule socket 320 on the other pole segment. A lower tether collar 322 is fixed inside lower pole segment 314 with epoxy, glue, or a weld, or by means of a press fit between the outside diameter of lower tether collar 322 and the inside diameter of lower pole segment 314. Lower tether collar 322 is fixed onto tether 306 with tether collar set screws 310, preventing tether 306 from sliding inside lower tether collar 322. Tip 106 is attached to the lower end of lower pole segment 314 by means of a press fit or threaded connection.

The sliding interface between sliding tube 300 and upper pole segment 304 allows the motion necessary to collapse and extend the probe in the following manner. When the device is in the collapsed position as shown in FIG. 3B, the user can place one hand on handle 102, and the other on upper pole segment 304, and slide them away from each other. This motion removes the slack in tether 306 between pole segments, causing ferrule cone 318 to guide ferrule 316 into ferrule socket 320. When the motion is complete, each ferrule cone 318 and ferrule 316 sits inside the ferrule socket 320, forming a connection between pole segments in a similar manner as many collapsible tent poles and avalanche rescue probes. When the user wishes to collapse the device, they must simply slide handle 102 and upper pole segment 304 towards each other, which returns the slack in tether 306 between the pole segments, allowing the user to fold the device at the exposed sections of flexible tether 306. Tether 306 helps contain the collapsed device as a single unit, easing storage and handling of the collapsed device.

The components shown in FIG. 3A and FIG. 3B can be made of, but not limited to, plastic, aluminum, steel, stainless steel, and titanium. In embodiments where pole 100 is electrically conductive, an electrical ground can be connected to upper pole segment 304 such that the ground continues all the way to tip 106. This helps shield tether 306 from external sources of electrical noise. Additionally, the electromechanical contacts created when pole 100 is extended can be used as a switch to turn the device on.

Figure 3C:
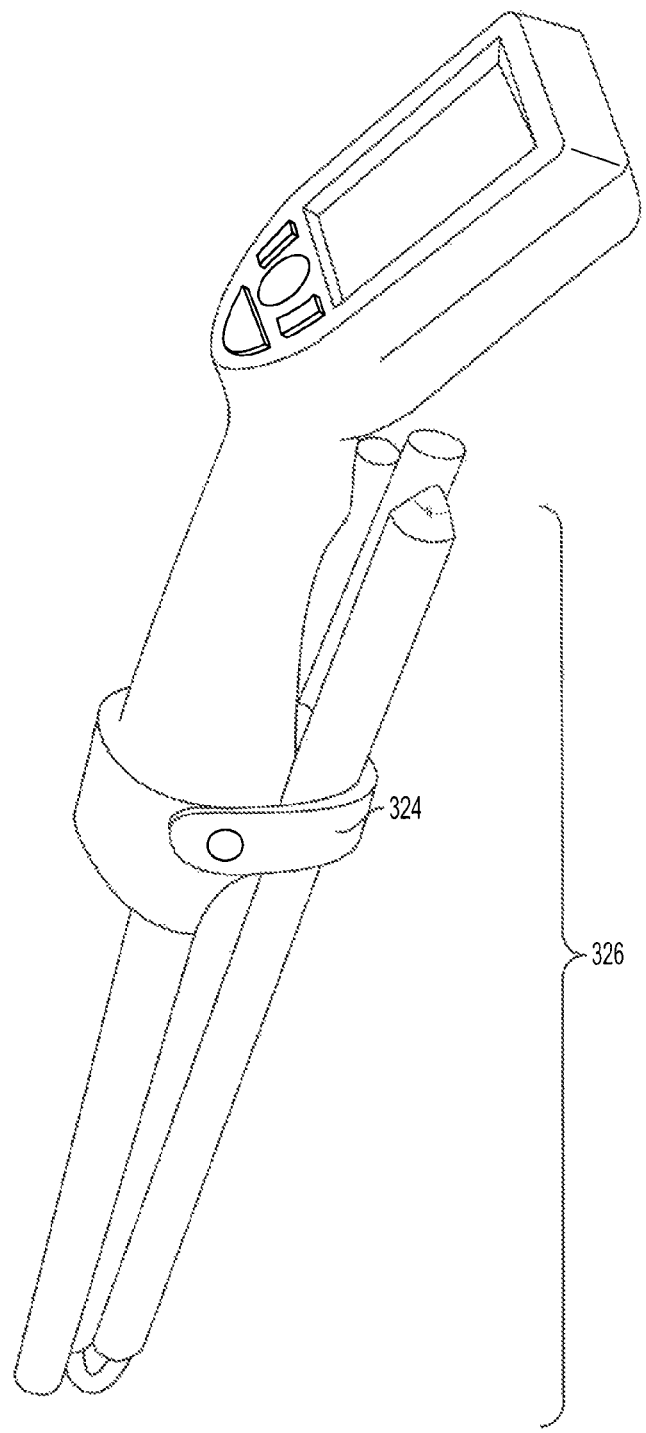
FIG. 3C is a close-up diagram depicting an example snow-measurement device in its collapsed position, according to embodiments of the present disclosure.

FIG. 3C shows an exemplary embodiment for bundling the device together in the collapsed position for ease of transport and storage. An elastic strap 324 at the bottom of the handle 102 can be wrapped around the pole bundle 326 to contain them and keep the entire collapsed unit together.

Figure 4:
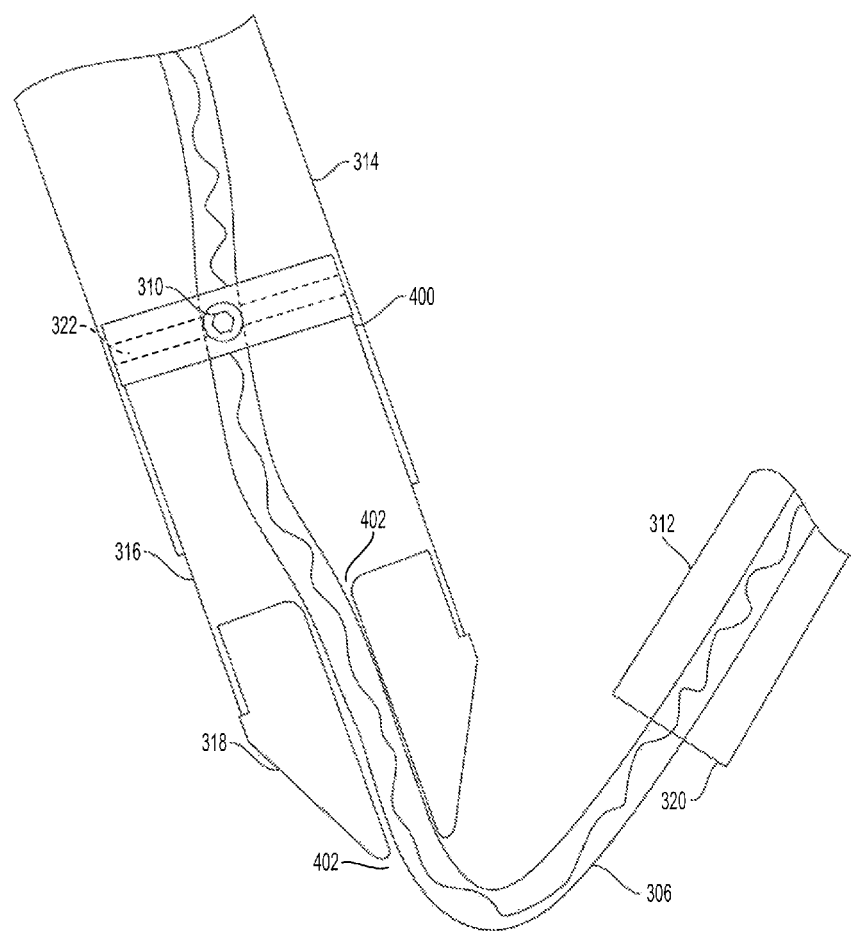
FIG. 4 is a diagram of the interface between the lower pole segment and the lower-mid pole segment of an example snow-measurement device, according to embodiments of the present disclosure.

FIG. 4 is a close-up view of the interface between lower pole segment 314 and lower-mid pole segment 312, according to some aspects of the present disclosure. Ferrule 316 provides a tether anchor mechanical stop 400 for lower tether collar 322. As described above, the glue/weld/press-fit connection between lower tether collar 322 and lower pole segment 314 prevents the lower tether collar from sliding towards the tip due to force transmitted by compression of tether 306, which can be small compared to force pulling lower tether collar 322 away from the tip due to the tension force in tether 306. Instead of designing the glue/weld/press-fit connection tolerate this large tension force, the glue/weld/press-fit between ferrule 316 and lower pole segment 314 can be used, where the lower end of the ferrule functions as a tether anchor mechanical stop 400. Curved tether interfaces 402 are shown on ferrule cone 318, which help prevent abrasion and wear on the tether at these sliding and bending interfaces.

Figure 5:
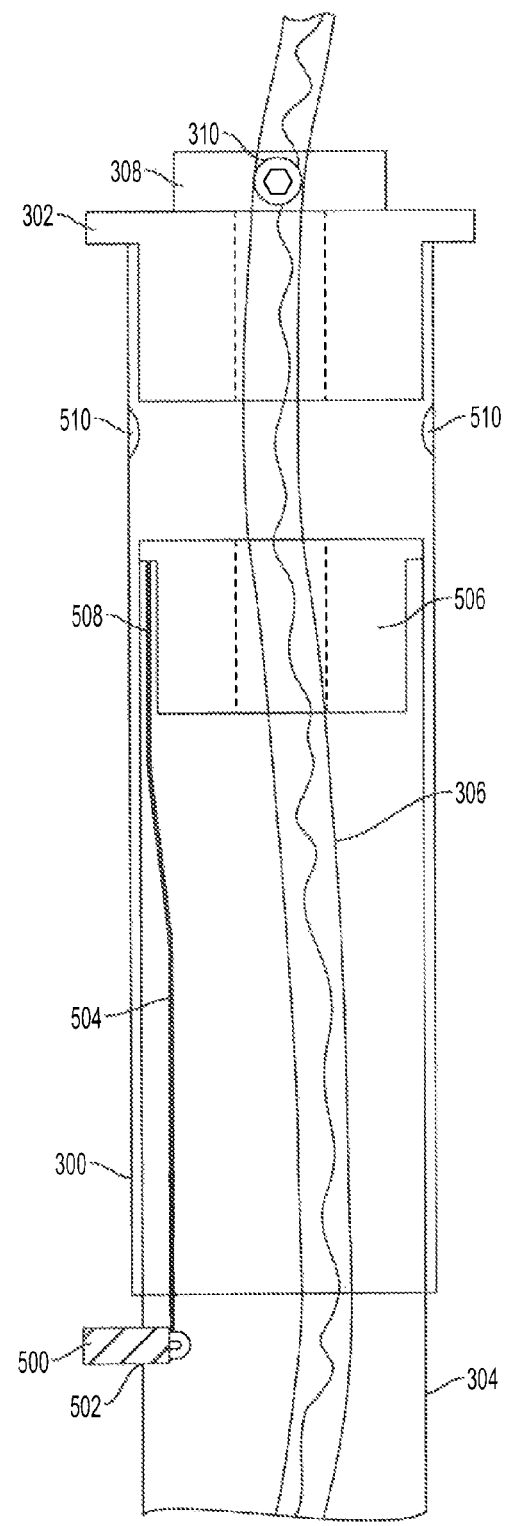
FIG. 5 is a diagram of the locking mechanism incorporated into the top of an example snow-measurement device's pole and handle when the device is in its extended position, according to embodiments of the present disclosure.

FIG. 5 shows a feature for locking the sliding mechanism described above so that the device remains extended or collapsed throughout use, according to some aspects of the present disclosure. In some embodiments, a spring plug 506 can be attached inside the upper end of the upper pole segment 304 by press-fit, adhesive, or a weld. A spring plug flat 508 is a feature on spring plug 506 that accommodates a spring arm 504, which is fixed in place by press-fit, adhesive, or a weld. At the lower end of the spring arm 504 is a spring button 500, attached by adhesive, nut and bolt, or a weld. This secures the assembly of spring plug 506, spring arm 504, spring button 500, and upper pole segment 304 such that the center of spring button 500 is located at the center of a spring button hole 502 on upper pole segment 304. The spring arm is held in place at the interface between spring plug 506 and upper pole segment 304. Finally, a locking indent group 510 is a feature in the sliding tube 300 ½ inch or less below the lower face of flanged stop 302.

At the end of the sliding motion to extend the device, sliding tube 300 clears the spring button 500 at the end of the sliding motion, allowing spring button 500 to pop through spring button hole 502. This is possible because spring arm 504 is pre-bent to cause it to exert a radially outward force on spring button 500. The user is then only able to collapse the device if he pushes the spring button 500 in while sliding the handle 102 towards upper pole segment 304. Without this locking mechanism, handle 102 and top pole segment 304 could slide towards each other while the user pushes the device into the snowpack, resulting in the device's collapse and making data collection difficult. Because of the cold-weather use case of this invention, the spring button should be large enough to use with gloved hands (³⁄₁₆ inch or greater diameter).

As mentioned above, to collapse the device, the user pushes in spring button 500 and then slides handle 102 and upper pole segment 304 towards each other. Sliding tube 300 then slides over spring button 500, thereby disengaging the locking mechanism. When the collapsing sliding motion is complete, locking indent group 510 squeezes the upper part of upper pole segment 304, resulting in enough friction to lock the device in the collapsed position. This is convenient because it maintains the collapsed position while the user folds the device at the sections of exposed tether 306 and transports the device between test locations.

Spring arm 504 can be made of an elastic material such as spring steel, and an exemplary material for spring button 500 is stainless steel. Exemplary materials for the other parts introduced in FIG. 5 are high strength aluminum or steel, chosen for machinability, strength, corrosion resistance, moderate cost, and high strength to weight ratio.

Figure 6:
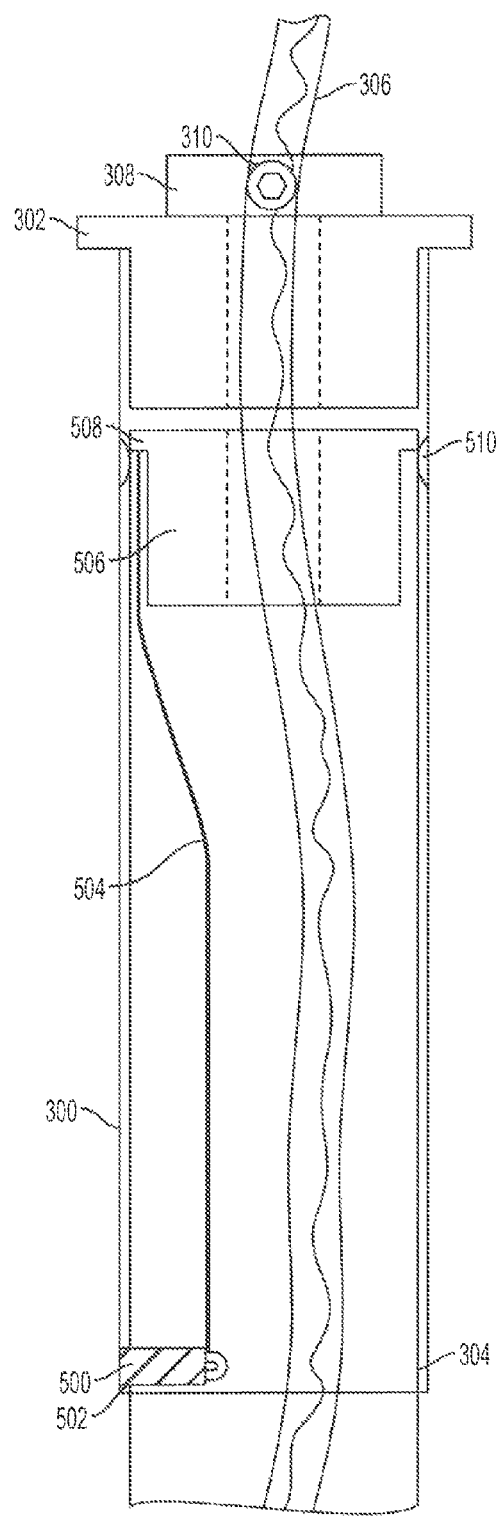
FIG. 6 is a diagram of the locking mechanism incorporated into the top of an example snow-measurement device's pole and handle when the device is in its collapsed position, according to embodiments of the present disclosure.

FIG. 6 is a close-up schematic view of the sliding/locking mechanism while collapsed, according to some aspects of the present disclosure. Here, sliding tube 300 covers spring button 500, and locking indent group 510 maintains the mechanism's collapsed configuration during user handling and transport.

The locking spring button mechanism described above is preferred over traditional spring buttons because it creates enough clearance inside upper pole segment 304 to accommodate tether 306. Additionally, the way spring arm 504 is anchored at the upper part of upper pole segment 304 is an easier assembly process than anchoring spring arm 504 at the location of spring button hole 502. The collapsing mechanism described above requires three inches or more of sliding motion so that there is enough slack to slip pole segments out of each ferrule 316, and the length of spring arm 504 can easily be adjusted to meet this specification. More traditional spring buttons don't allow this flexibility in location, or provide enough clearance for tether 306 in such a small diameter tube.

Figure 7:
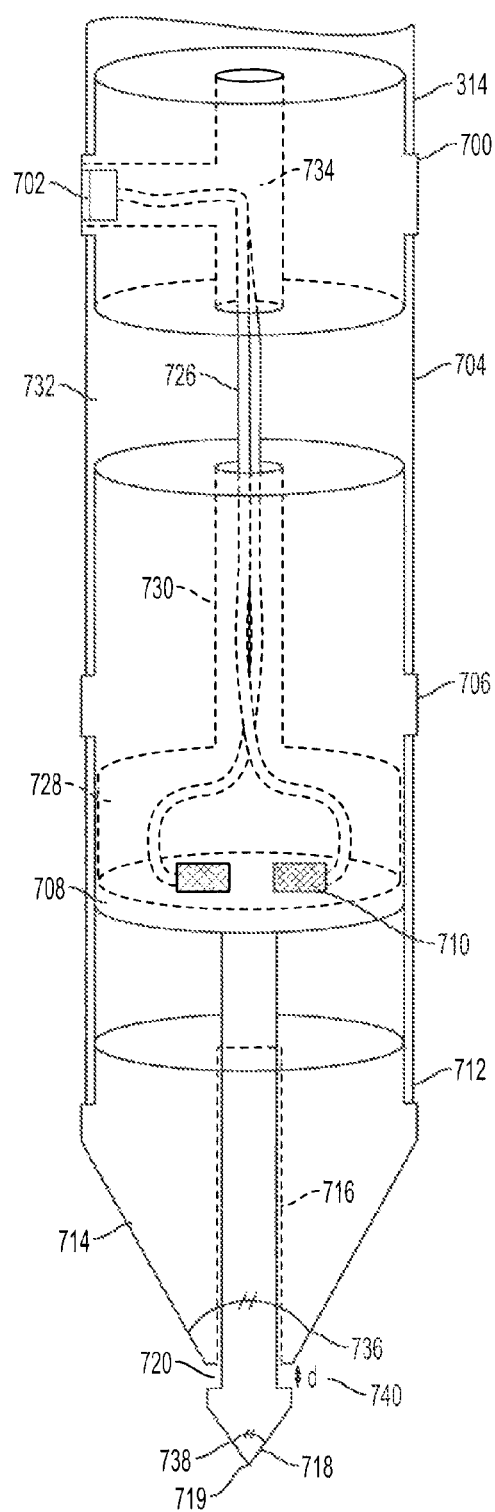
FIG. 7 is a diagram of the tip of an example snow-measurement device incorporating a force sensor comprising a load cell diaphragm, according to embodiments of the present disclosure.

FIG. 7 shows tip 106 and its associated components, according to some aspects of the present disclosure. Lower pole segment 314 connects to a plastic, rubber, metal, or composite damping connector 700 by press fit, threads, adhesive, or a weld. A snowpack temperature sensor 702 or other snowpack measurement sensor can be incorporated into the damping connector 700. Onto the lower portion of damping connector 700 is connected a tip pole segment 704, which is connected by press fit, threads, adhesive, or a weld. Tip pole segment 704 connects to a tip connector 706 by press fit, threads, adhesive, or a weld. Tip connector 706 is also a suitable location for temperature sensor 702 or other snowpack measurement sensors. In the lower portion of tip connector 706 is a load cell cavity 728. A load cell diaphragm 708 is fixed inside the rim of load cell cavity 728 by press fit, adhesive, or a weld such that it covers the lower end of load cell cavity 728. Onto one of the faces of load cell diaphragm 708 one or more strain gauges 710 are mounted. A tip sheath 712 fixes over the end of tip connector 706 by press fit, adhesive, threads, or a weld. A tip cone 714 fixes into the other end of tip sheath 712. A tip cylinder 716 can be a cylindrical hole running through the center axis of the tip cone 714. A resistance sensing element 718 can be a cylindrical shaft that ends in a conical tip 719. Slightly above conical tip 719 the diameter of the resistance sensing element 718 can be reduced to create an overload bumper 720. The resistance-sensing element 718 continues as a cylindrical shaft that slip-fits inside the tip cylinder 716. The upper end of the resistance-sensing element 718 can attach to the load cell diaphragm 708 by press fit, weld, adhesive, or threads. They could also be machined out of the same piece of stock, or 3D printed/laser sintered. Force sensors can be strain gauge or piezoelectric based force transducers.

When the device is pushed through the snowpack, varying amounts of resistance from different snow layers apply a force on conical tip 719. This force is transmitted through resistance-sensing element 718 and onto load cell diaphragm 708. This force strains load cell diaphragm 708, resulting in elongation or compression of strain gauges 710. This strain causes a change in the electronic signal leaving strain gauges 710 that flows through load cell wires 726. Load cell wires 726 travel through load cell cavity 728, and then through a tip connector hole 730. They can then emerge into a damping cavity 732 before passing into a damping connector hole 734. Any wires from the snowpack temperature sensor 702 or other snowpack measurement sensors mounted in the damping connector 700 also travel through the damping connector 700 and enter the inside of lower pole segment 304. Here, all wires associated with tip 106 can connect to tether 306, resulting in an electrical connection between handle 102 and sensors in tip 106.

A cone internal angle 736 of tip cone 714 and a tip internal angle 738 of conical tip 719 can be 60 degrees or less to decrease the magnitude of resistance caused by a given snow layer. This is possible because penetration resistance decreases as the internal angle of a cone penetrometer tip decreases. This can make it easier for the user to penetrate the snowpack where hard layers are present, as well as minimize variations in penetration speed caused by the varying hardness encountered by tip 106. The cone internal angle 736 can be further decreased below 60 degrees to prevent tip cone 714 from compressing the snow in front of it.

Resistance sensing element 718 and other components between the snow and strain gauges 710 can be lightweight to minimize inertial forces sensed by the snowpack resistance sensor 104. Minimizing this mass can also reduce the resonant frequency of the force sensing system and therefore allow for a higher sampling rate and snowpack measurement resolution. Because robustness is also important for resistance sensing 718 element, high strength aluminum, titanium, or stainless steel are possible materials. The maximum diameter of conical tip 719 affects the minimum layer thickness that can be measured by the device. If the internal angle of the conical tip 719 is small, or if the maximum diameter of the conical tip 719 is large, the thickness of snow affecting the snowpack resistance sensor increases. Some diameter should be chosen based on minimum desired layer resolution. For avalanche safety uses, the device uses a conical tip 719 diameter of 0.3125 inches or less. This diameter should not be completely minimized (below 0.1 inches for instance), because small local variations in the snowpack can be expressed if the diameter is on the order of such variations. In case local variations do affect test results, the device includes a way of probing several times in the same location and averaging the results to produce a more representative snow profile.

A tip offset distance 740 can be set to bring conical tip 719 out in front of the lower face of tip cone 714. This design can help the device maintain a constant speed through snow layer interfaces. Because conical tip 714's and pole 100's cross-sectional areas are several times larger than the cross-sectional area of resistance sensing element 718, the majority of the resistance is provided not by the resistance sensing element 718, but instead by the overall pole diameter. As a user pushes the device through the snowpack, changes in resistance due to different snow layers can make it difficult for the user to penetrate at constant speed. For instance, as the device breaks through a hard layer and enters soft snow, acceleration occurs. It may be beneficial to measure the transition from one layer to the next at a constant speed instead of while accelerating. If the tip offset distance 740 is greater than zero, conical tip 719 can enter the next layer while tip cone 714 is still in the other layer above it. This allows tip cone 714 to help regulate penetration speed while conical tip 719 senses ahead of tip cone 714 so that it can measure layer transitions at near constant speed.

Damping connector 700 is an optional feature that can be incorporated to isolate tip 106 from any vibrations in the other parts of the device. When not incorporated, lower pole segment 314 can connect directly to tip connector 706 by press fit, adhesive, threads, or a weld, eliminating the need for damping connector 704. Any snowpack measurement sensors embedded in damping connector 700 could then be embedded in tip connector 706 instead. Additionally, tip connector 706 can be made of rubber, composite, plastic, or another material with damping characteristics to help isolate the lower parts of tip 106 from vibrations in the upper device.

Figure 8A:
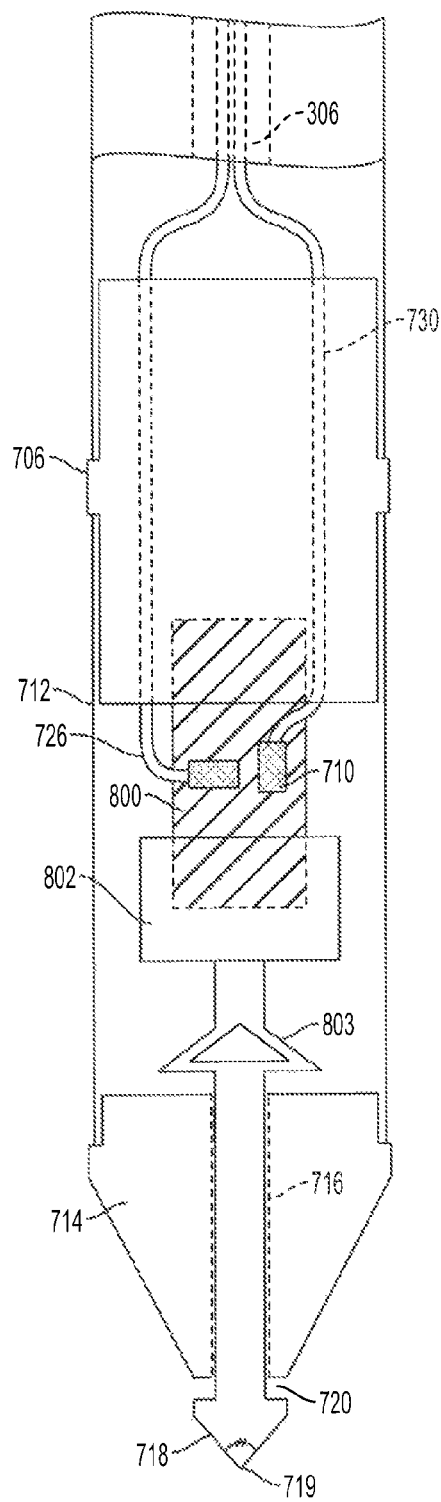
FIG. 8A is a diagram of the tip of an example snow-measurement device incorporating a force sensor comprising a load cell cylinder, according to embodiments of the present disclosure.

FIG. 8A shows an alternative embodiment for the force sensing mechanism described in FIG. 7. Damping connector 700 is not shown in this figure. Instead of load cell diaphragm 708, a load cell cylinder 800 connects to a cylinder force transmitter 802, which then connects to resistance-sensing element 718. Strain gauges 710 can be mounted on the exterior surface of load cell cylinder 800, or cast inside load cell cylinder 800.

The resistance from the snowpack results in a force on the resistance-sensing element 718, which can act to compress load cell cylinder 800 along an axis parallel to lower pole segment 314 and expand elongate load cell cylinder 800 along an axis perpendicular to lower pole segment 314. This results in a change in the electronic signal leaving strain gauges 710.

The overload bumper 720 can prevent the resistance-sensing element 718 from displacing so much that it damages more delicate parts above it, such as the load cell cylinder 800 or load cell diaphragm 708. These delicate components measure force because of elastic deformation, and if force continues into the plastic deformation regime, the device's force sensing mechanism can break and need replacement. To prevent this from happening, tip 106 is designed such that resistance-sensing element 718 can receive much more force than would normally damage these parts. When a certain force is applied to the resistance-sensing element 718, overload bumper 720 contacts tip cone 714 and prevents any further displacement that could damage components inside tip 106. The exact force and displacement at which overload bumper 720 engages tip cone 714 can be tuned by rotating the resistance-sensing element and changing how far onto load cell diaphragm/cylinder force transmitter 708/802 it threads. Doing this changes the zero-load distance between overload bumper 720 and tip cone 714. Finally, changing the stiffness of load cell diaphragm 708 or load cell cylinder 800 can determine the force in the system when overload bumper 720 contacts tip cone 714. Most OEM load cells experience very little displacement (0.003 inches or less) at maximum load, requiring that this displacement adjustment be equally subtle. Such tolerances are expensive and difficult to achieve in multi-part assemblies like this one. To simplify this matter, load cell diaphragm 708 can be a specific material and geometry such that it experiences more displacement at maximum load without yielding (i.e. a material that yields at higher strain). For instance, a spring steel or plastic diaphragm of the right thickness can result in maximum load displacements of 0.025 inches or more. This can ease the tolerances required to protect tip 106 from overloading, because the zero load displacement can then be on the order of 0.025 inches (or less) instead of 0.003 inches. Additionally, if resistance sensing element 718 threads into the load cell diaphragm/cylinder force transmitter 708/802, simply twisting it changes the zero-load distance between overload bumper 720 and tip cone 714, which allows post-assembly fine-tuning of the force at which overload protection engages. Additionally, the threading allows resistance-sensing element 718 to be completely removed from the device, a convenient feature if the tip needs cleaning, replacement, or other maintenance.

If additional displacement is needed to achieve overload protection, a spring can be added in series anywhere between where the snow contacts the conical tip 719 and where the force sensor attaches to the mechanical ground of the tip 106 (i.e. the tip connector 706). This can give the sensor assembly compliance at the expense of reducing its resonant frequency. A possible embodiment of this concept is shown in FIG. 8A, according to some aspects of the present disclosure, where the resistance sensing element 718 includes a compliant flexure 803. This reduces the stiffness of the mechanism that carries snowpack resistance to the force sensor, therefore resulting in larger displacements for a given applied force. Compliant flexure 803 could be substituted for a compression spring for the same result.

Figure 8B:
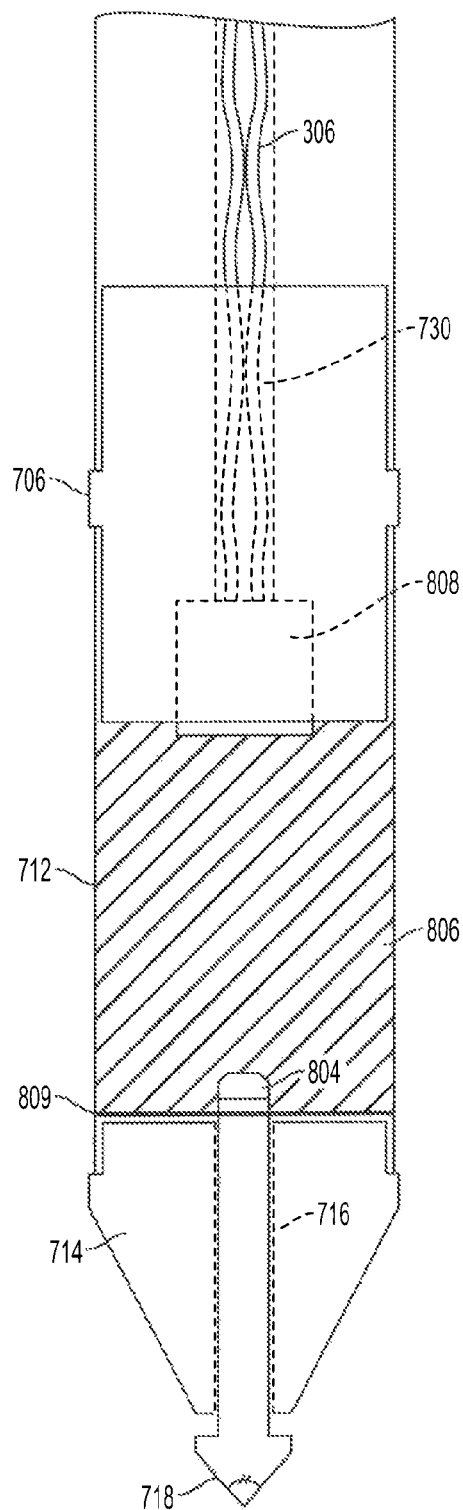
FIG. 8B is a diagram of the tip of an example snow-measurement device incorporating a force sensor comprising a pressure cavity and pressure sensor, according to embodiments of the present disclosure.

FIG. 8B shows an alternative embodiment for the snowpack resistance sensor 104, according to some aspects of the present disclosure. Here, resistance sensing element 718 has a blunted upper end 804 that ends inside a pressure cavity 806 between tip cone 714 and tip connector 706. Force from the snow results in an increase in pressure inside pressure cavity 806, and this change in pressure is measured by a pressure sensor 808.

Pressure cavity 806 can be filled with anything that exhibits viscous or visco-elastic behavior such as a polymer, oil, or gel. Polymers and gels have an advantage over a liquid because they hold their shape, requiring no need for a fluid seal to prevent it from leaking out of the pressure cavity 806. However, liquid has the advantage that it has zero shear modulus, so the weather-proofing seal described in FIG. 11 (below) can be used to prevent liquid from leaking. A seal can also be created by use of a metal bellows or a sealing diaphragm 809 connected to the end of the outside diameter of the resistance sensing element 718 and the inside diameter of the tip cylinder 716 or inside diameter of the pressure cavity 806. This sealing diaphragm should be thin (and therefore compliant) enough to allow enough displacement to adequately pressurize pressure cavity 806 from typical snowpack resistance pressures (approximately 0-3 MPa).

Figure 8C:
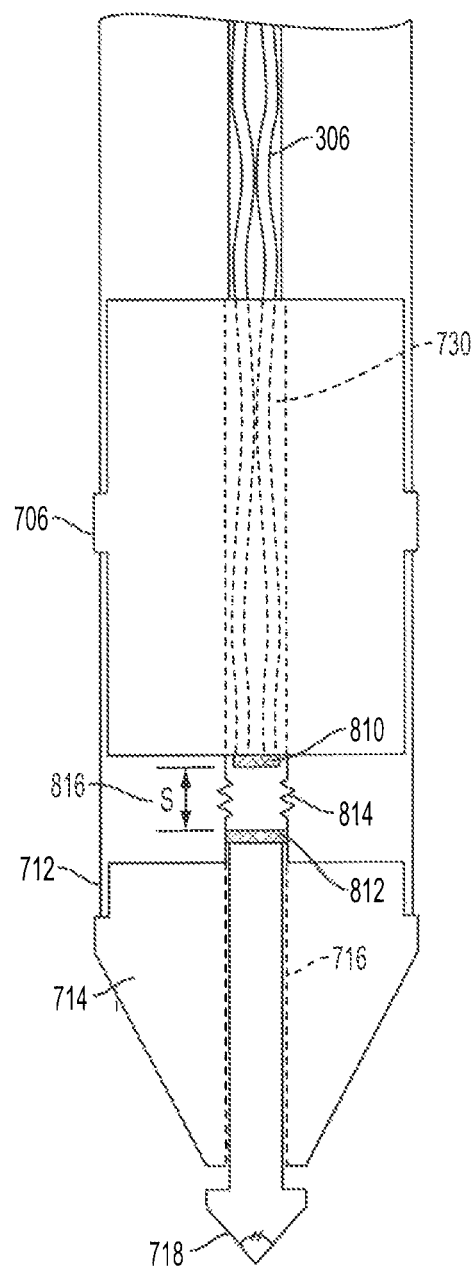
FIG. 8C is a diagram of the tip of an example snow-measurement device incorporating a hall effect sensor, a compression spring, and a magnetic upper end, according to embodiments of the present disclosure.

FIG. 8C shows another embodiment for snowpack resistance sensor 104, where a hall effect sensor 810 and a compression spring 814 are used together to create a force sensor, according to some aspects of the present disclosure. Here, resistance sensing element 718 can have a magnetic upper end 812. Compression spring 814 can be in parallel with the hall effect sensor 810 (mounted onto tip connector 706) and the magnetic upper end 812. Force from the snowpack can compress compression spring 814, which reduces sensed displacement 816 (S) between magnetic upper end 812 and the hall effect sensor 810. Hall effect sensor 810 can measure sensed displacement 816 because the motion of the magnetic upper end 812 changes the magnetic field measured by hall effect sensor 810. Similarly, other displacement sensor in parallel with a spring could be used to create a force sensor. Possible other displacement sensors include a linear variable differential transformer (LVDT), a capacitance sensor, or a position sensitive diode. Additionally, instead of axial compression spring 814 shown in FIG. 8C, a cantilever or diaphragm can be used to create a spring between the target (in this case, resistance sensing element 718) and the sensor.

Figure 9:
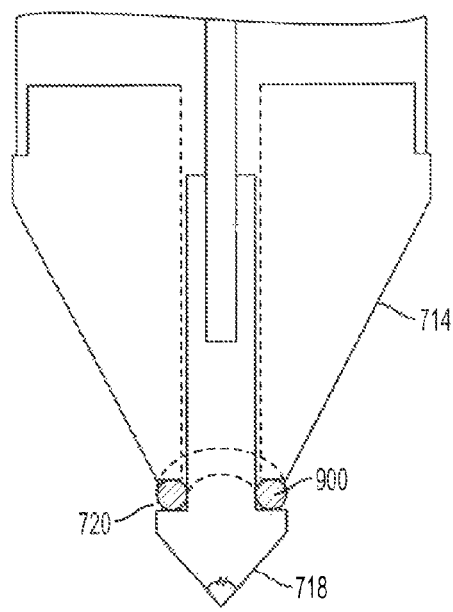
FIG. 9 is a diagram of the tip of an example snow-measurement device incorporating a weather o-ring, according to embodiments of the present disclosure.

FIG. 9 shows a way of sealing the tip 106 with a weather o-ring 900, according to some aspects of the present disclosure. Weather sealing is important because it can prevent water, snow, ice, and other debris from entering the assembly and adding friction between resistance-sensing element 718 and tip cylinder 716. The electronics in the tip (i.e. strain gauges 710) should also be protected from contaminants. Weather o-ring 900 sits between overload bumper 720 and the lower surface of tip cone 714. Weather o-ring 900 should not be pre-loaded by resistance-sensing element 718, because this would make any forces smaller than the pre-load force immeasurable by the device (the preloading re-directs force away from the force sensor and into tip sheath 712.

Figure 10:
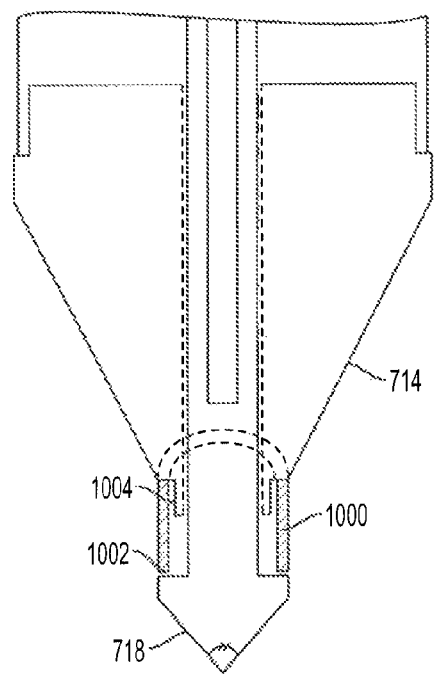
FIG. 10 is a diagram of the tip of an example device incorporating a weather tubing, according to embodiments of the present disclosure.

FIG. 10 shows an alternative embodiment for weather sealing that uses a piece of tubing (weather tubing 1000) instead of weather o-ring 900, according to some aspects of the present disclosure. Weather tubing 1000 rests between overload bumper 720 and lower surface of tip cone 714. To accommodate the thickness of weather tubing 1000, grooves 1002 and 1004 are cut out of resistance-sensing element 718 and tip cone 714, respectively.

Figure 11:
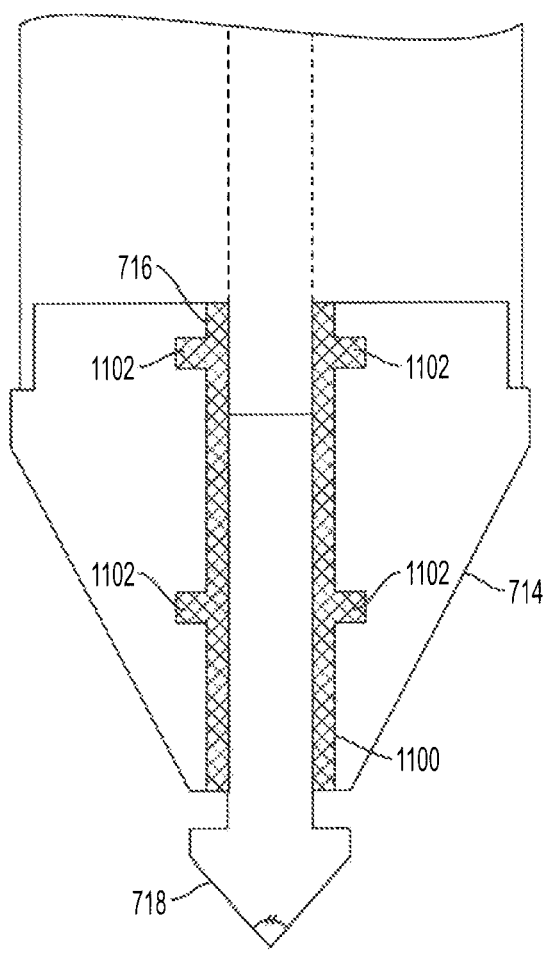
FIG. 11 is a diagram of the tip of an example snow-measurement device incorporating a weather-proof filler, according to embodiments of the present disclosure.

FIG. 11 shows another embodiment for weather sealing tip 106, where weather sealing is done with a filler 1100 approach, according to some aspects of the present disclosure. Filler 1100 fills the space between tip cylinder 716 and resistance-sensing element 718. Fixture grooves 1102 can be added to the inside of tip cylinder 716 to prevent the filler from slipping inside tip cylinder 716. Alternatively (or in addition), internal threads on tip cylinder 716 could be added, as well as external threads on resistance sensing element 718. Resistance sensing element 718 and filler 1100 do not slide relative to one another, but the filler 1100 is able to deform and allow displacement of resistance sensing element 718 necessary for transmitting force to the load cell above it. Filler 1100 can be a cast polymer, allowing it to fill the void space as a liquid before curing into a soft, deformable solid. Silicone polymers may be suitable because their properties are less sensitive to temperature changes than many other polymers.

A similar seal can also be created by placing o-rings or annular pieces of a soft rubber between resistance sensing element 718 and tip cylinder 716 (as opposed to pouring polymer to incorporate the rubber seal).

Figure 12A:
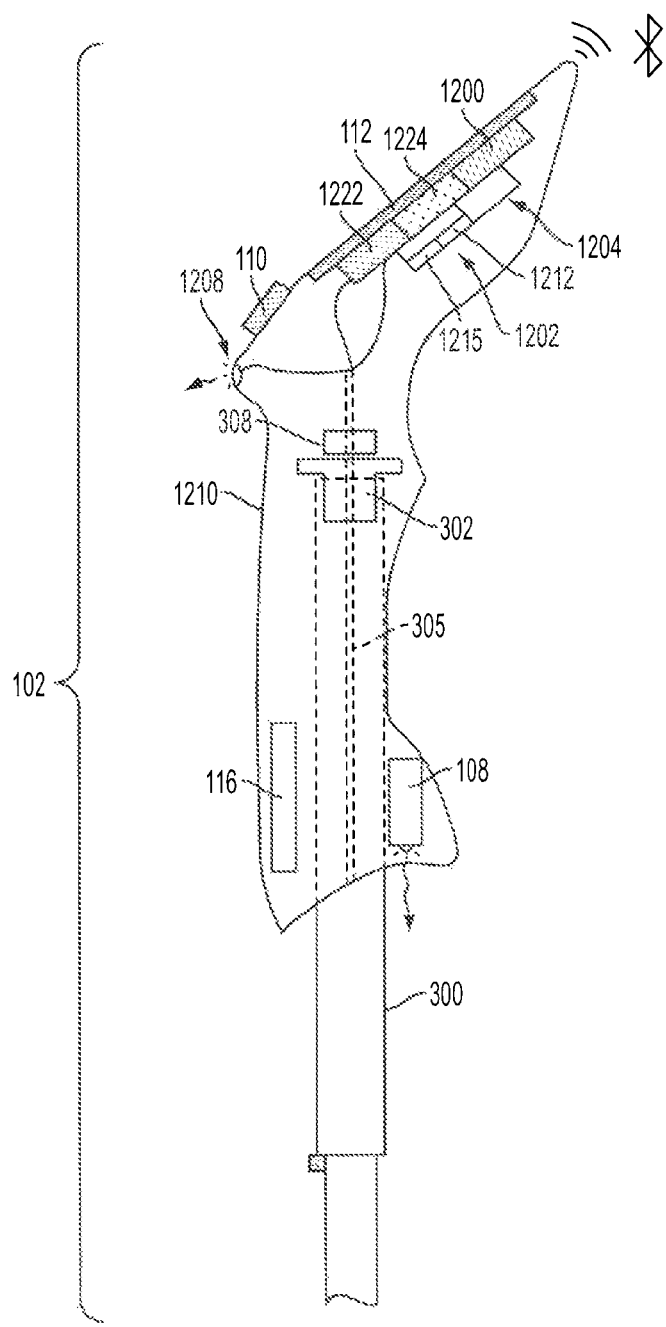
FIG. 12A is a side view of the handle of an example snow-measurement device and its associated components, according to embodiments of the present disclosure.

FIG. 12A shows handle 102 and its associated components, according to some aspects of the present disclosure. Inside handle 102 is a microcontroller 1200, a memory subsystem 1222, a snowpack measurement subsystem 1224, an environmental measurement subsystem 1202 which may include some or all of the following: a GPS block 1212, inclinometer (not shown), a tilt-compensated compass 1215, ambient temperature sensor (not shown), altimeter (not shown), and humidity sensor (not shown), and an external communication subsystem 1204 containing some or all of the following: USB port (not shown), WiFi module (not shown), and Bluetooth module (not shown). Display 112 can be visible on the exterior of handle 102. A user interface light emitting diode (UI LED) 1208 is also visible to the user as she holds the device by a grip 1210 (or alternatively, a UI tone can be audible to the user). Buttons 110 are accessible by the user when she is holding the grip 1210. Handle 102 also can include power supply 116, range-finding snow depth sensor 108, sliding tube 300, flanged stop 302, upper tether collar 308, and upper end of the tether 306.

Handle 102 serves as a place for the user to hold the device, as well as housing for the electronics that aren't located in tip 106. A GPS block 1212 in handle 102 automatically stores the location of each test. The user can link each test to the slope's inclination by holding the device parallel to the slope and holding the inclinometer button before the test start button is pressed. Similarly, the user can face downslope and hold the aspect button to store that aspect with the subsequent test. If neither of these measurements are taken before a test, the test can simply lack aspect and inclination information.

Each of buttons 110 should be large enough to press with a gloved hand, and a watertight gasket can be placed around each button to prevent water and other contaminants from entering handle 110.

Note that UI LED 1208 can be replaced or combined with a UI tone, such that the information is conveyed as an auditory signal.

Figure 12B:
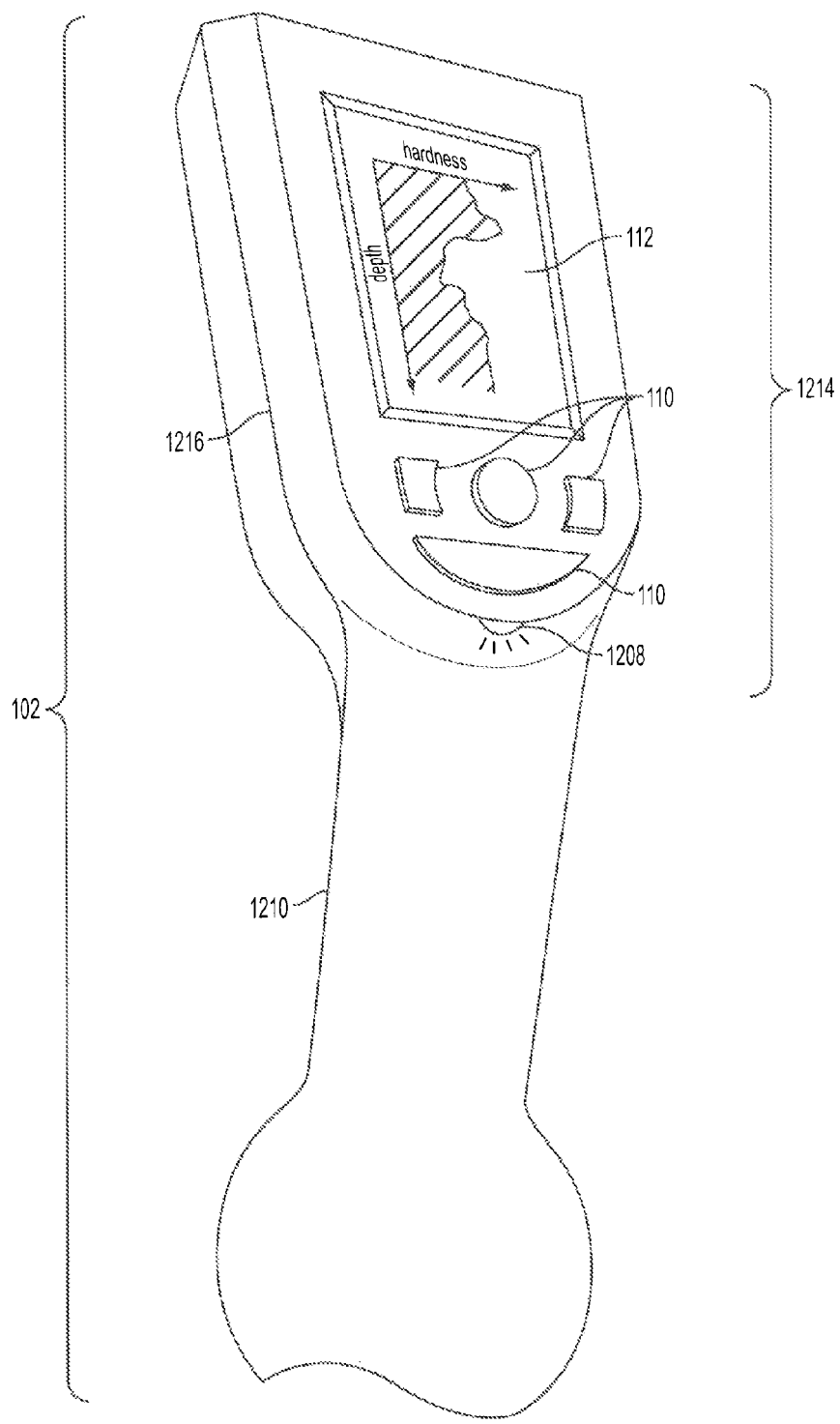
FIG. 12B is a front view of the handle of an example snow-measurement device and its associated components, according to embodiments of the present disclosure.

FIG. 12B is a schematic illustration of handle 102 and associated user interface, according to some aspects of the present disclosure. The user interface is managed by microcontroller 1200, which communicates to the user via display 112 and UI LED 1208. The user is then able to navigate user interface 1214 by pressing buttons 110. Buttons 110 enable the user to start a test, look at prior test results, power the device on/off, and view other information managed by the microcontroller.

Handle 102 can be made of two or more main pieces, and a handle parting line 1216 between them can be seen in FIG. 12B. Each piece comes together around sliding tube 300 to contain it, and parting line 1216 makes assembly possible while ensuring that sliding tube 300 cannot leave the handle once the two handle halves are fixed together with glue, screws, snap-fit, ultra-sonic weld, or other means.

Figure 12C:
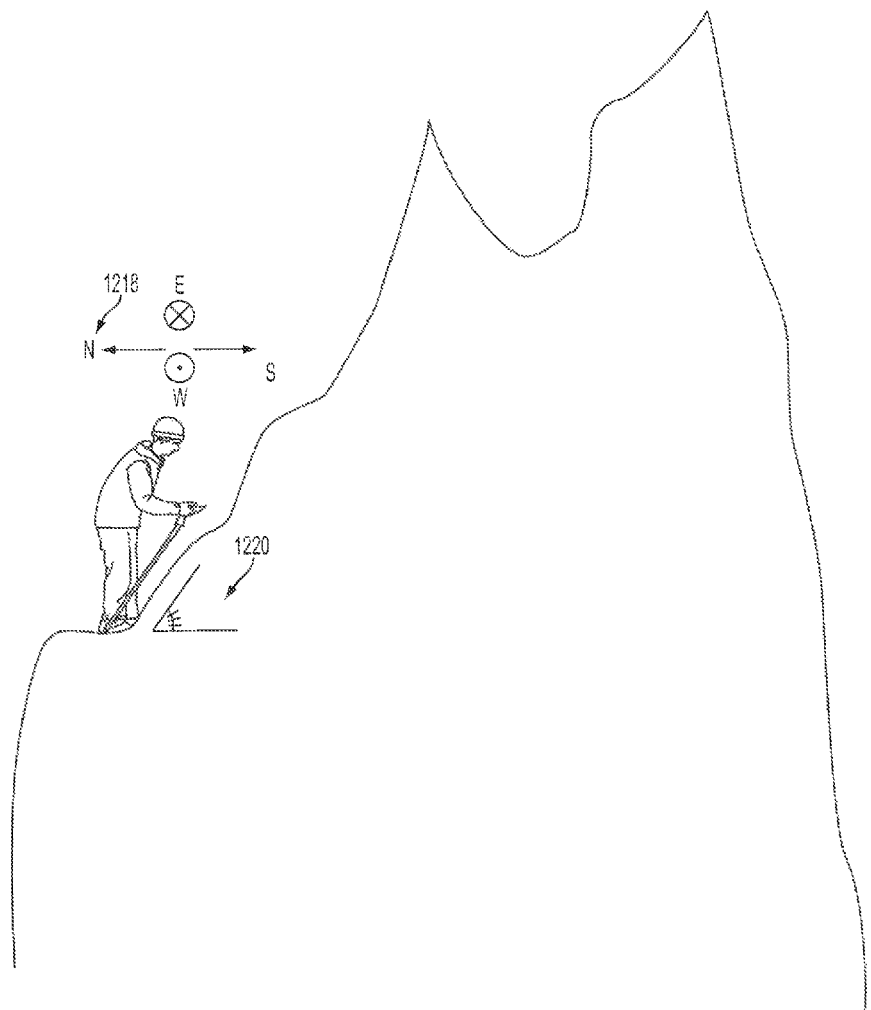
FIG. 12C is an illustration of the difference between slope aspect and slope inclination, according to embodiments of the present disclosure.

FIG. 12C shows how the incorporation of a tilt-compensated compass 1215 can be used to measure slope aspect 1218 (i.e., which direction the slope is facing) and inclination 1220 in the same step, according to some aspects of the present disclosure. The slope aspect and inclination can be collected simultaneously by laying the probe on the snowpack facing directly uphill and holding a button to initiate data collection, and releasing it when the measurements have been taken. This is possible because the tilt-compensated compass 1215 (see FIG. 12A) can make an accurate compass reading even when the device is not parallel to the ground. In addition to bearing, the tilt-compensated compass 1215 records pitch and roll, which can be used to derive inclination.

Figure 13:
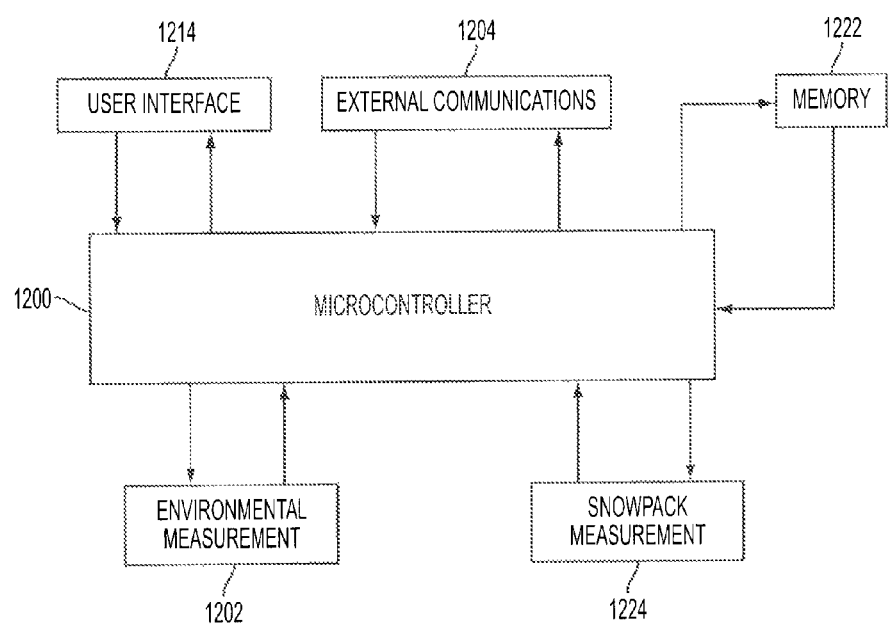
FIG. 13 is a block diagram of an example snow-measurement device's electronic subsystems, according to embodiments of the present disclosure.

FIG. 13 is a block diagram of an embodiment of the device's electronics, according to some aspects of the present disclosure. Microcontroller 1200 is connected to the user interface 1214, an external communications subsystem 1204, a memory subsystem 1222, an environmental measurement subsystem 1202, and a snowpack measurement subsystem 1224.

Microcontroller 1200 can pull data from memory subsystem 1222 and transmit it to a mobile device (e.g., a smartphone or tablet), computer, or associated web database via external communications subsystem 1204. This is possible because of WiFi, Bluetooth, and USB port modules embedded in handle 102. Memory subsystem 1222 can be any digital storage system, such as an SD card, micro SD card, hard drive, or other system.

Microcontroller 1200 can also record and show environmental data via user interface 1214 by reading the outputs of the device's environmental measurement sensors in its snowpack measurements subsystem 1224, which may include components such as, but not limited to: a humidity sensor, an altimeter, a GPS block, an ambient temperature sensor, an inclinometer, and tilt-compensated compass. Snowpack measurements subsystem 1224 may also be responsible for managing the functions of snowpack resistance sensor 104, snowpack temperature sensor 702, snow depth sensor 108, and a snow grain type or grain size sensor (not shown). Unlike the snowpack temperature sensor 702, the ambient temperature sensor discussed above is configured to measure the temperature of the local ambient atmosphere and not the temperature of the snow layer. However, the functions of the ambient temperature sensor may also be performed by snowpack temperature sensor 702.

Figure 14:
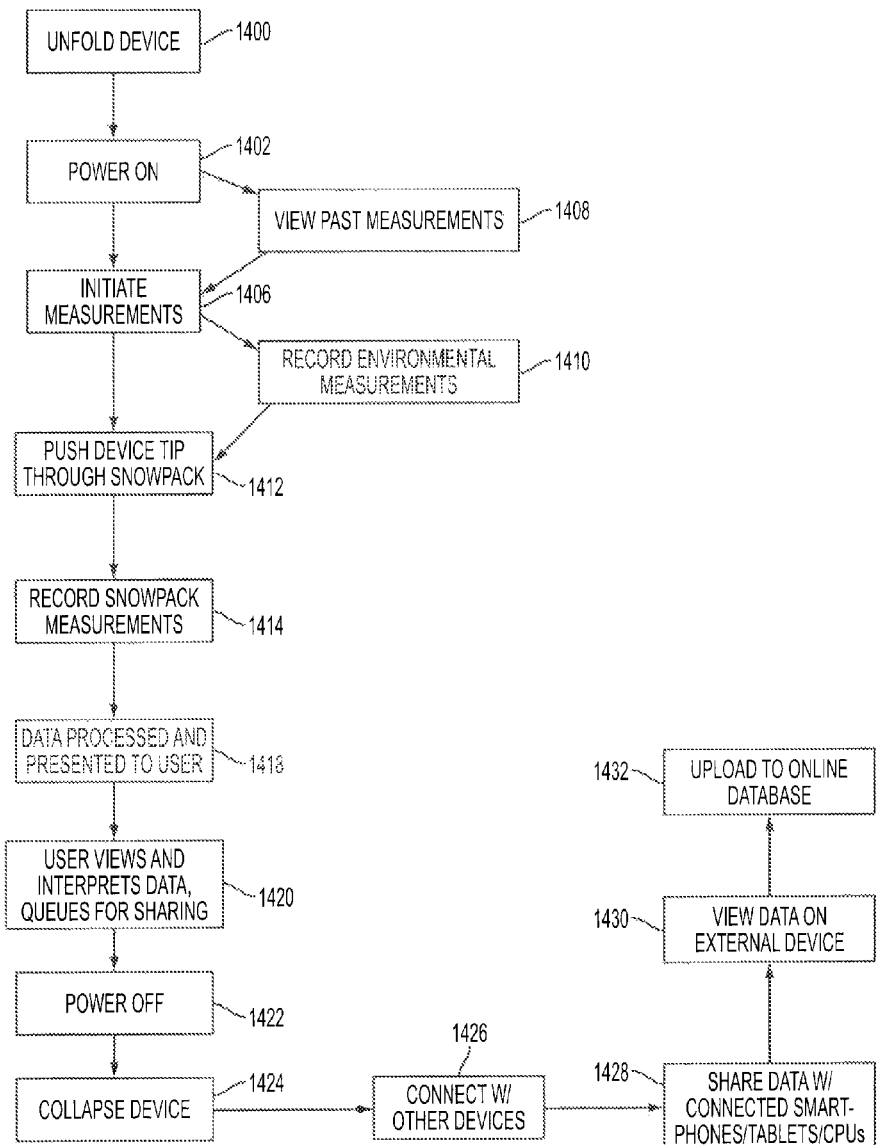
FIG. 14 is a flow-chart depicting the process for using an example snow-measurement device, according to embodiments of the present disclosure.

FIG. 14 is a flow chart of the steps to use the device, according to some aspects of the present disclosure. The user can first unfold the device 1400 and slide the sliding tube 300 to lock the pole in extended position. Holding the power button to power on 1402 the device can be done before or after unfolding the device. Once powered, the user interface is used to initiate measurements 1406 via the environmental/snowpack measurement subsystem, or to view past measurements 1408 that are stored in the device's memory subsystem. Via the user interface, users can optionally have the device record environmental measurements 1410 such as, but not limited to, GPS location, temperature, relative humidity, inclination, and slope aspect. The user can also push the device tip through the snowpack 1412 to record snowpack measurements 1414. The microcontroller receives the user's request through button inputs, and then directs the environmental/snowpack measurement subsystem to sample from their associated sensors. This data is stored in the device's memory subsystem. From there, the microcontroller processes the data in step 1418 as described by FIG. 17 and presents the processed data to the user via the display, which is part of the user interface. The user can interpret the data and press one of the buttons to queue that test to be shared 1420 with another device that connects to the device via its external communication subsystem (it is also possible for the user to set the device to automatically queue every test for upload). The user can repeat these steps as many times as they wish, and then collapse and power off the device by holding one of the buttons. Powering off 1422 is done by holding the power button. The device can be collapsed 1424 by pushing the spring button and sliding the sliding tube into the handle. An automatic power-off can occur if none of the buttons are pressed for one minute (the user can adjust this time setting). Test results may be transmitted to a user's mobile device (e.g., a smartphone or tablet). Test results can include any measurement taken by the device, including, without limitation, a profile of snow hardness as a function of depth, a profile of snow temperature as a function of depth, a profile of grain size as a function of depth, local ambient temperature, humidity, slope aspect, or inclination. A mobile device may include a display screen, a memory, a short-range communication module for sending and receiving data over a short-range wireless link (e.g., Bluetooth, WiFi, or NFC) or over a wired connection, and a long-range communication module configured to communicate with a central server via a wireless network. Test results may also be transferred to a user's personal computer, which also may include a display, a memory, a processor, and a short-range communication device. Once the user establishes a wireless or wired connection in step 1426 with their mobile device or computer, any test queued to transfer can automatically be shared with connected devices in step 1428 and can then be viewed on the external device in step 1430 (even if the connection is subsequently broken). Next, any shared data can then be uploaded to an online database in step 1432 for further data analysis, mapping, and interpretation. The exact remaining steps to transfer information to the database (and the database's features) are described in a later section.

In addition to the steps outlined above, the user has the option to measure the snowpack temperature profile in a separate or concurrent step. While a fast-acting snowpack temperature sensor 702 could be incorporated into tip 106 such that the temperature profile is recorded at the same time as the hardness profile, an embodiment of the device can measure temperature in a different step. The user holds one of buttons 110 to enter snowpack temperature measurement mode, and display 106 can direct them to put tip 106 just beneath the snowpack surface 204. When the slow-acting snowpack temperature sensor 702 has acquired a temperature measurement, the device may direct the user to slowly penetrate several centimeters using any of an indicator on display 106, an audible tone from a speaker integrated into the device, a sequence of flashes from UI LED 1208, a haptic device configured to vibrate the handle 102, or any other notifications means known in the art. Once the user has reached new depth 200, display 106, an audible tone from the speaker, a sequence of flashes from UI LED 1208, a vibration from the haptic device and/or some other notification means can signal the user to stop until a stable temperature measurement has been taken. This process can repeat until the user has pushed the pole 100 as far as possible through the snowpack. The temperature profile can then be graphed on the display 106 and interpreted by the user.

In addition to the steps outlined above, the user has the option to measure the snow grain size of the layers of the snowpack in a separate or concurrent step. A small camera and light source can be incorporated into the tip 106 that records images of the snow surface as the device penetrates the snowpack. The user can then view these images, along with the depth at which they were taken to see how the snow grains change throughout the snowpack. Another possible way of determining grain size is to use information from the snowpack resistance sensor, where an adequately high sample rate (at least 5 samples per mm) will show changes in the snowpack's resistance to penetration resulting from the loading and rupture of individual bonds between snow grains (Schneebeli, M., C. Pielmeier, and J. Johnson. "Measuring Snow Microstructure and Hardness Using a High Resolution Penetrometer." *Cold Regions Science and Technology*. 30. 1-3 (1999): 101-114.).

Figure 15:
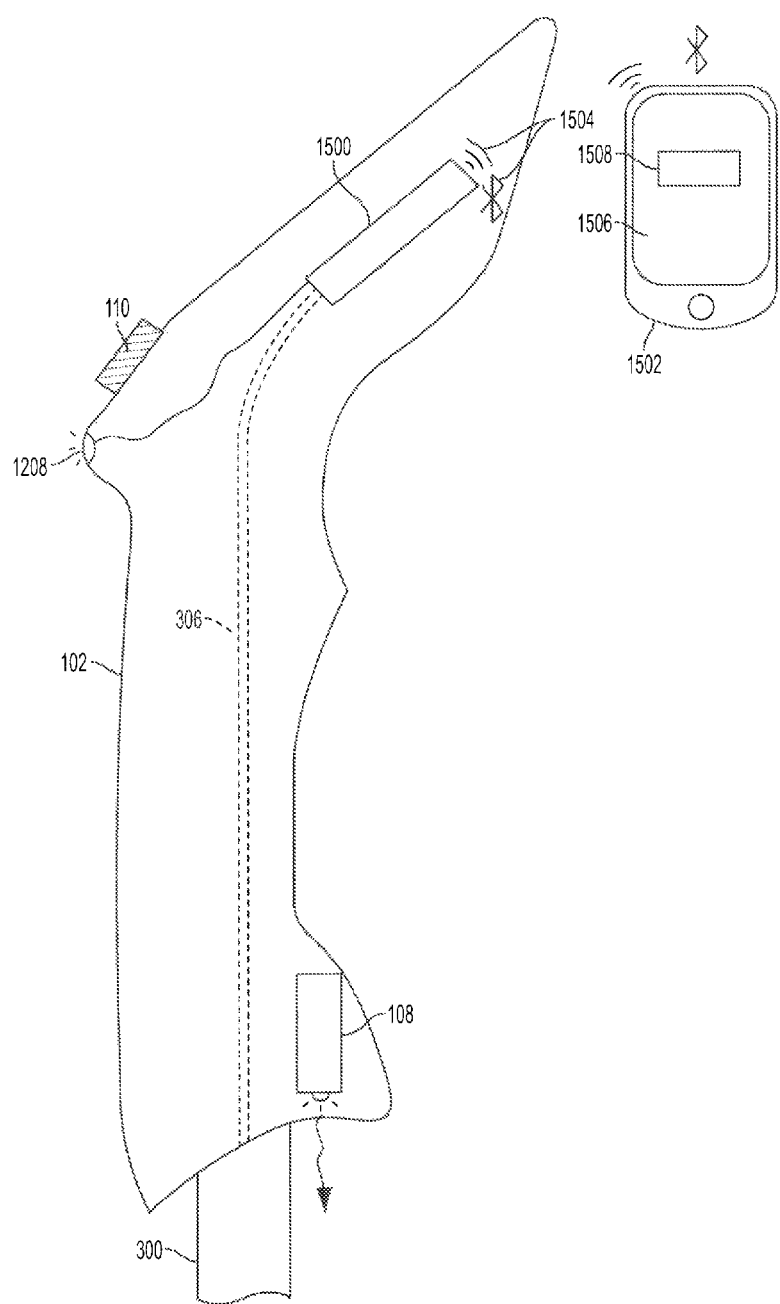
FIG. 15 is a diagram of an example snow-measurement device that uses an external mobile-device (e.g., a smartphone) for a screen instead of including a display on the snow-measurement device itself, according to embodiments of the present disclosure.

FIG. 15 shows an embodiment where an external mobile device (e.g., a smartphone) 1502 can be used for the screen instead of including display 106 on the device itself, according to some aspects of the present disclosure. The mobile device 1502 may be similar to the mobile device described above in relation to FIG. 14. Handle 102 still contains a microcontroller based data acquisition, signal processing, and external communications subsystem 1204, and external communications modules such as Bluetooth or WiFi modules 1504 are used to send mobile device 1502 information to be displayed. The user is able to control the information on a mobile device display 1506 by pressing buttons 110 on the handle, or buttons integrated into the mobile device application 1508.

Figure 16:
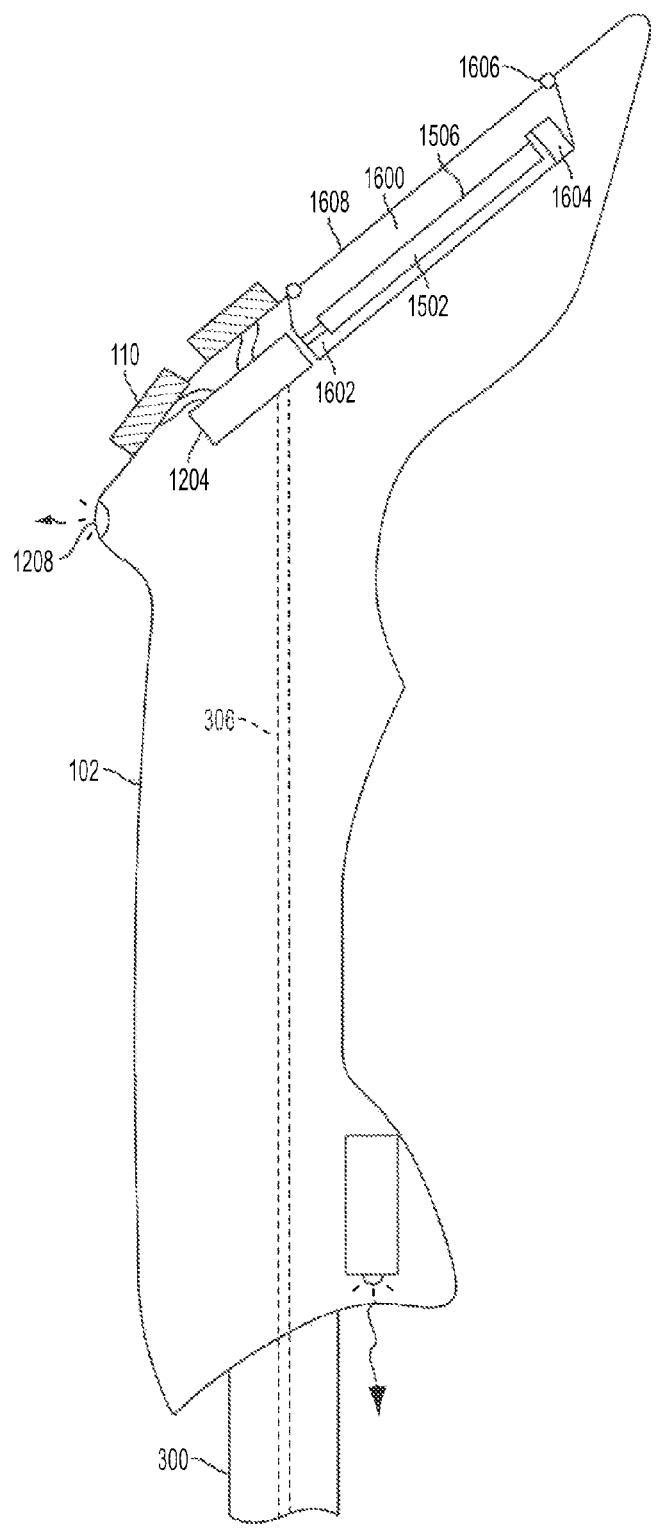
FIG. 16 is a diagram of an example snow-measurement device that includes a mobile-device mount inside the handle, according to embodiments of the present disclosure.

FIG. 16 shows an alternative embodiment with a mobile-device mount located inside handle 102, according to some aspects of the present disclosure. A mobile device housing 1600 covers the mobile device with a mobile device-viewing window 1608, and provides a mobile device clamp 1604 to hold mobile device 1502 in place. The microcontroller based data acquisition, signal processing, and external communications subsystem 1204 can wirelessly communicate with mobile device 1502, or connect directly via mobile device connector 1602. Mobile device-viewing window 1608 opens at window hinge 1606, allowing the user to place her mobile device 1502 in mobile device housing 1600. The user can operate the device and navigate the mobile device user interface by pressing buttons 110 on handle 102. UI LED 1208 can provide a way of notifying the user of a test in progress (and other states of the device) that doesn't require looking at mobile device display 1506.

These two embodiments that use a mobile device 1502 reduce the cost and size of the device. Mobile device 1502 can also be charged via the mobile device connector 1602.

Figure 17:
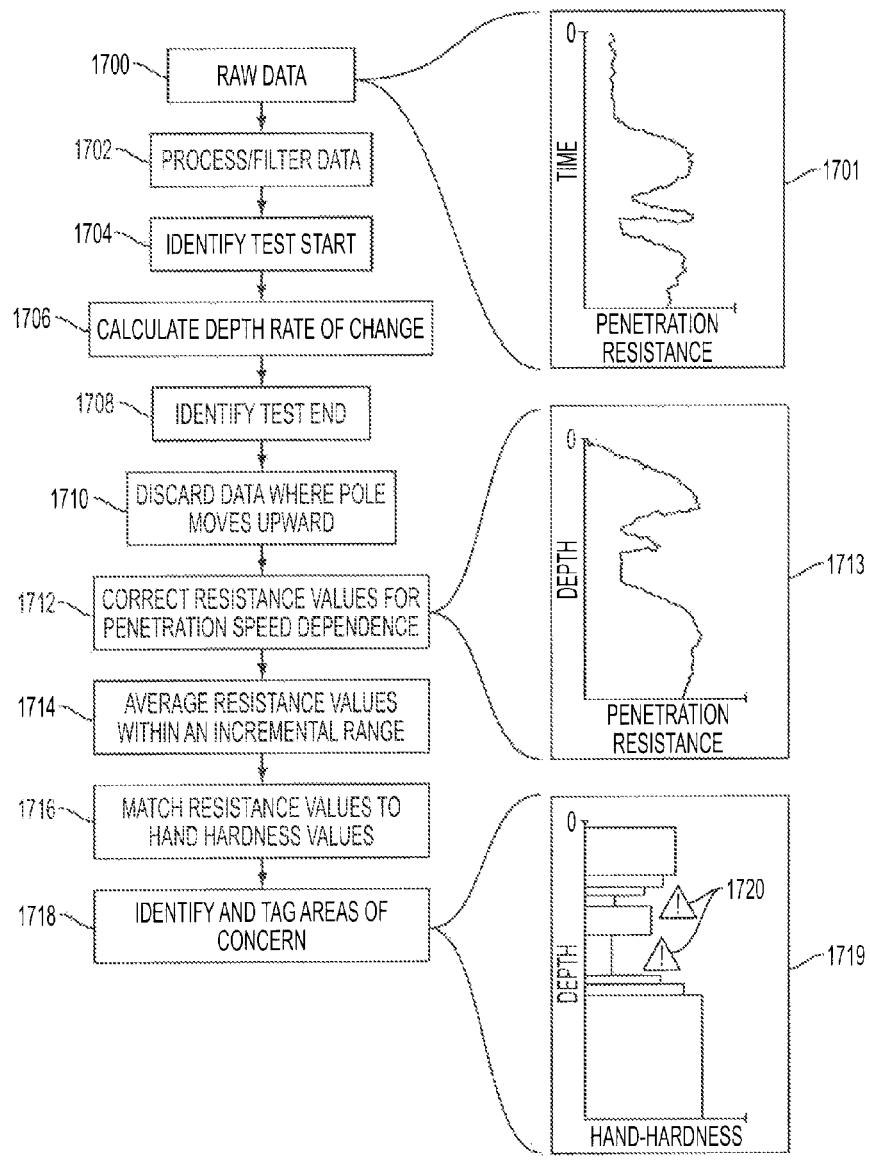
FIG. 17 is a flow-chart depicting the data processing algorithms used by an example snow-measurement device to derive snow stratigraphy from raw penetration data, according to embodiments of the present disclosure.

FIG. 17 is an overview of data processing algorithm used to show snow stratigraphy from raw penetration resistance data, according to some aspects of the present disclosure. A version of the raw test data 1700 can be saved to the device's memory subsystem 1222. The raw data can be plotted to display 112 as penetration resistance vs. time as shown by 1701 in FIG. 17. To derive penetration resistance with respect to depth rather than time from the raw test data 1700, the first step can be for the microcontroller 1200 to process and filter 1702 the data with averaging, median filters, and exponential smoothing. Next, the microcontroller 1200 can identify the test start 1704 by the test start trigger from the snowpack resistance sensor 104. If either optical trigger 210 or optical flow sensor 208 are present on the device, they can also be used to detect the exact moment when the device penetrates the snowpack, and so identify the test start 1704. All data points collected before the test start 1704 can be discarded so that the start coincides with a depth equal to zero. Next, the depth rate of change 1706 can be calculated by looking at the relative change between each successive depth reading. The test end 1708 can be identified because it coincides with the last collected data point that shows depth was still increasing. Alternatively, the test end 1708 can be identified if the rate of change between each successive depth reading is below a certain threshold for a predetermined period of time, i.e., the device has stopped moving. From here, any data points where the depth rate of change 1706 shows that the tip 106 was moving out of the snowpack and not deeper than the previous point can be discarded 1708. At this point, the data can be saved as a new version.

Considering the sampling rate and depth rate of change 1706 allows for the calculation of average penetration speed between depth measurements. This calculated penetration speed can be used to correct each penetration resistance value for penetration resistance's dependence on penetration speed by using a lookup table developed experimentally. This version of speed-corrected snowpack penetration resistance vs. depth 1712 can be saved to the memory subsystem 1222, and plotted to the display 112 as trimmed and calibrated data 1713.

Next, the speed-corrected snowpack data 1712 can be filtered for easier visual interpretation. In order to display snowpack penetration resistance vs. depth data in a way widely accepted by the avalanche safety community, steps can be taken to show more discrete layers than seen in the trimmed and calibrated data 1713. Penetration resistance values that are within approximately 10% of each other can be averaged to filter out the subtle, yet unimportant variations detected by the snowpack resistance sensor 104 (averaging shown as step 1714 in FIG. 17). Any large change in snowpack resistance can be greater than this 10% window, and hence significant hardness transitions can be preserved. After this averaging is complete, the resistance values can be compared to the standard hand-hardness values accepted by the avalanche safety community by use of a lookup table (shown as step 1716 in FIG. 17). The lookup table can be generated by experimentally collecting penetration resistance and hand-hardness data side by side. Finally, areas where the hardness decreases beyond a predetermined percentage (e.g., 50%) within a predetermined range (e.g., 10 cm) can be tagged as an area of concern 1720 (i.e., indicative of high avalanche risk). Users can have the option to adjust these parameters, including both the predetermined percentage and the predetermined range, based on their preferences. The smoothed data can then be plotted to the display 112 as shown in 1719. The trimmed and calibrated data 1713 and smoothed data 1719 can be superimposed and displayed simultaneously if desired. Smoothed data 1719 therefore constitutes a profile of snow hardness as a function of depth.

In addition to the data processing outlined above, a correlation analysis can be done to show how closely a given test resembles one of the 10 snow hardness (resistance) profiles developed by Schweizer and Lütschg in Switzerland (Schweizer, J. and M. Lütschg. 2000. Measurements of human-triggered avalanches from the Swiss Alps. Proceedings International, Snow Science Workshop, Big Sky, Mont., U.S.A., 2-6 Oct. 2000). This can help the user understand the snow packs he measures, because comparison to these well understood ten profiles allows the user to benefit from the extensive studies performed by Schweizer and Lütschg. As new snow profile data is collected, these ten profiles can be re-developed, and new profiles can be added to this correlation test.

While the data processing steps discussed above with regard to FIG. 17 relate to measuring snow stratigraphy, they can also be applied to measuring a profile of snow layer temperature according to depth, and snow grain size according to depth. For example, the start of tests directed at measuring a profile of temperature and depth may be triggered by resistance sensed by snowpack resistance sensor 104, optical trigger 210 or optical flow sensor 208. Similarly, the end of such tests may also be identified as coinciding with the last collected data point that shows depth still increasing. Raw temperature and grain size data can also be smoothed, filtered and averaged in the manner described above, as well as compared with experimental values as described above. Finally, areas in the temperature and grain size data indicative of an increased avalanche risk can be tagged as an area of concern potentially using the same or similar algorithms as described above.

In addition to the hardware device, this disclosure relates to a unique data sharing system to further enhance backcountry safety and avalanche forecasting. Each time measurements are taken with the hardware device, the data is recorded both on the device and automatically shared via Bluetooth and WiFi to a mobile-device application (or other electronic communication device). Data includes a snow profile, slope inclination, slope orientation, time, GPS coordinates, temperature gradient, and more. The device and mobile device application also pull in external data on local weather, recent snowfall, etc. Additional computer software allows users to view data and move data to and from the hardware device.

Data transported to the mobile device application or computer software from the hardware device is stored on a server where it can be accessed remotely by a computer or other mobile device devices. Subscribers to the data services can be able to see all of the data acquired from users of the hardware device in real-time and historically. Sharing this data across a broad network has the potential to create one of the largest sets of information on critical avalanche risk metrics in the world. With an innovative mobile device application and web portal that allow users to access local, regional, and global data, this information can improve decision making of individual backcountry adventurers as well as forecasting methods of ski resorts, mines, avalanche forecast centers, guides, and other snow professionals.

Another benefit of a shared data network is that users can be able to view snowpack and other local measurement from other users in their vicinity or far away, further informing their decisions through the backcountry. For example, one user planning to go to a certain backcountry area may notice multiple measurements from other users in the same location earlier that day. If the measurements convey dangerous information, this individual may be able to decide not to go without ever even setting foot on the slope.

Furthermore, geolocation data integration with mobile mapping and GIS technologies can allow aggregation of historic avalanche data to form cold and hot zones of avalanche activity—this can be viewed at any time, not only by individual users but also for scientific and weather research purposes among others. The data can be mapped in one, two, or three dimensions and can even help professionals identify weak areas within the snowpack which may be more effectively targeted by explosives, thereby improving avalanche control precision and reducing costs.

Lastly, for professionals and more advanced recreational users, a software package can allow users to download data from the device to their computer where they are able to do more complex snow science analytics.

Figure 18:
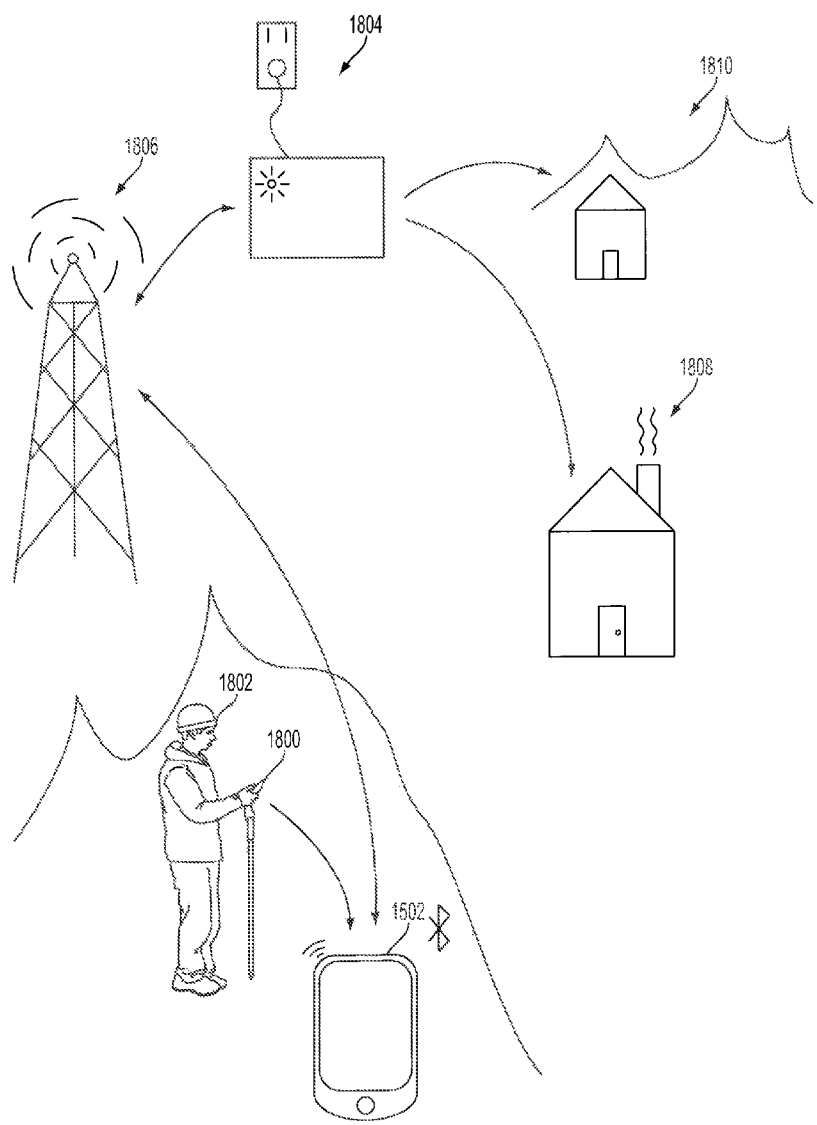
FIG. 18 is an illustration of the data flow from an example snow-measurement device to an online database and to remotely located users, according to embodiments of the present disclosure.

FIG. 18 shows the information flow for how the system sources data from the hardware device 1800 for the online database, according to some aspects of the present disclosure. Once the user 1802 has transferred test results from device 1800 to their mobile device 1502 as described in steps 1426 and 1428 of FIG. 14, mobile device 1502 can send test results to server 1804 via a wireless network transceiver 1806. As discussed above, test results can include any measurement taken by the device 1800, including, without limitation, a profile of snow hardness as a function of depth, a profile of snow temperature as a function of depth, a profile of grain size as a function of depth, local ambient temperature, humidity, slope aspect, or inclination. Server 1804, which may include at least a processor, an internal memory, and at least one interface for receiving and transmitting data, functions as a host for the data collected by the hardware device 1800 by storing the collected data in the internal memory for later retrieval. Server 1804 also can receive and record information regarding the source of the collected data, including a unique identifier corresponding to the source device 1800, a unique identifier corresponding to user 1802, the date and time the data was collected by device 1800, the date and time the data was received by the server 1804, and the geographical location corresponding to the collected data (i.e., where the test results were taken).

Server 1804 may receive similar test results and information from multiple users, perhaps simultaneously. Furthermore, server 1804 may also analyze information from a single user or from multiple users to draw inferences and conclusions about the degree of avalanche risk in a certain area. For example, if server 1804 detects that an anomalously large number of test results from in and around a specific geographic area indicate a high avalanche risk, server 1804 may determine that that specific geographic area poses a high avalanche risk. Server 1804 may also determine that a high avalanche risk exists for a geographic area for which it has not received any data by extrapolating from data received regarding neighboring geographic areas. Sever 1804 may also be configured to receive information from other information sources, such as weather-related information (e.g., temperature, humidity and/or wind-speed information) or alerts (e.g., snowfall warnings) from weather stations or sensors, and to factor in such information when determining the degree of avalanche risk for a specific geographic area. If server 1804 determines that a specific geographic area poses a high avalanche risk, server 1804 may be configured to proactively send an alert to, for example, users' mobile devices, weather forecasting centers, avalanche forecasting centers, ski resorts, alpine mines, departments of transportation, and other recipients. Alternatively, if server 1804 receives a safety warning published by avalanche forecasting centers or other information outlets, the server 1804 may forward the safety warning to all of the recipients listed above.

Other consumers can pull in data from the server 1804 via, for example, a mobile device 1502, which effectively allows users to share their data with others. Furthermore, avalanche forecasting centers 1808, ski resorts 1810, and other recipients (such as alpine mines, departments of transportation, etc.) can pull in the data stored on the server 1804.

Figure 19:
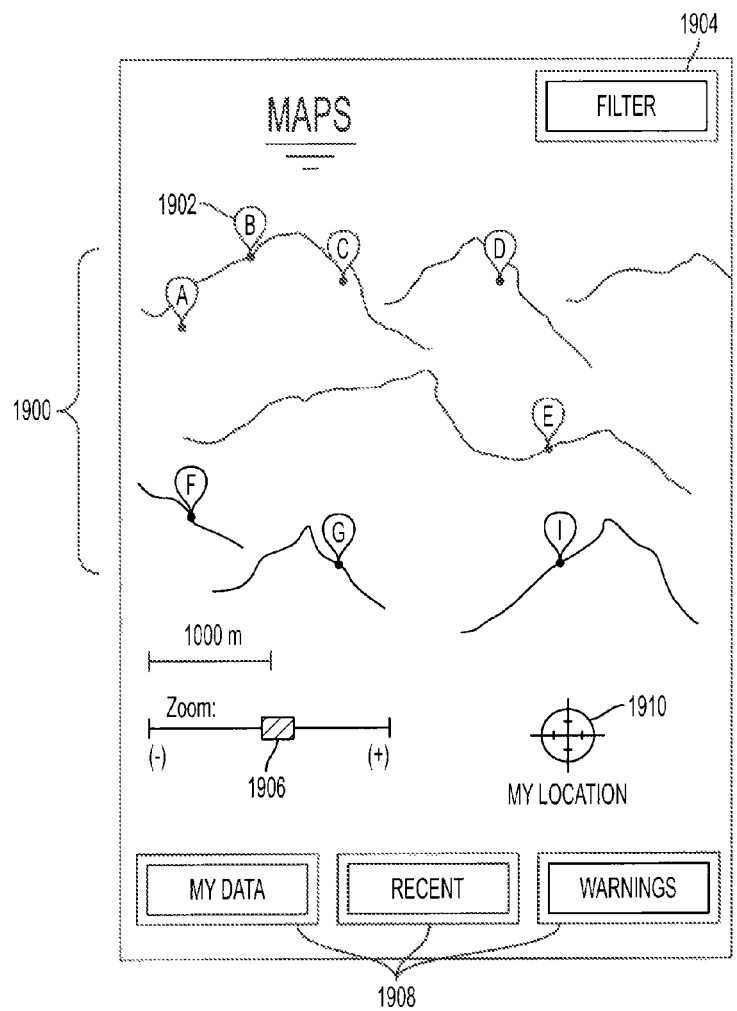
FIG. 19 is an illustration of a user interface for an example mobile-device-based application to view data collected by a snow-measurement device, according to embodiments of the present disclosure.

FIG. 19 shows an example user interface for a mobile-device-based application to view data collected by the device, according to some aspects of the present disclosure. The mobile-device-based application in this example may be capable of receiving test results directly from a user's snow-measurement device over a short-range communication link such as Bluetooth, WiFi or NFC, as described above. The mobile-device-based application in this example may also be capable of receiving test results from server 1804 over a wireless network, and sending test results to server 1804 over the wireless network. An area map 1900 is visible on the mobile device screen with markers 1902 indicating locations where device measurements have been taken. Markers 1902 may correspond to device measurements taken by the user's own device or to measurements taken by other user's which have been downloaded from server 1804. Users can press the filter button 1904 to filter the displayed results based on their associated metadata, such as user type (recreationalist vs. professional), time of measurement, altitude of measurement, and other parameters. Users also can be able to move the zoom slider 1906 to zoom in and out of the map, or press the my location button 1910 to jump to their current location. Sliding the map on a touch screen can also scroll to change the visible area. Quick access buttons 1908 shown at the bottom of FIG. 19 can be pressed to quickly view additional information accessible via the application, such as data collected by the currently logged-on user, most recent tests, or safety warnings published by avalanche forecast centers or other information outlets. Other interfaces can exist to show data in list form, and markers can be clicked on to show detailed snowpack information represented in ways as described by FIG. 17. A similar interface can also be accessed via a web application or tablet.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor can receive instructions and data from a read only memory or a random access memory or both. The essential elements of a computer are a processor for executing instructions and one or more memory devices for storing instructions and data. Generally, a computer can also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

The invention claimed is:

1. An apparatus for measuring snow structure and stability comprising:
    a pole having a length, a first end and a second end;
    a sensing unit located at the first end of the pole, the sensing unit comprising a head shaped for probing a layer of snow, the sensing unit configured to measure a size of snow grains within the layer of snow;
    a range sensor configured to measure a distance between the range sensor and a surface of the layer of snow; and
    a processor configured to
        determine a depth of penetration based on the distance measured by the range sensor and the length of the pole; and
        determine a profile of snow grain size according to depth based on the measured size of snow grains measured by the sensing unit.

2. The apparatus of claim 1, wherein the sensing unit comprises a camera configured to record images of the layer of snow.

3. The apparatus of claim 2, further comprising a data display screen configured to display the recorded images of the layer of snow.

4. The apparatus of claim 1, wherein the sensing unit comprises a snowpack resistance sensor configured to measure a resistance to penetration of the layer of snow.

5. The apparatus of claim 4, wherein the sensing unit measures the size of snow grains based on changes in the measured resistance to penetration resulting from loading and rupturing of individual bonds between snow grains.

6. The apparatus of claim 1, wherein the sensing unit comprises a tip cylinder, a resistance sensing element disposed within the tip cylinder, and a weather-sealing filler which fills a space between the resistance sensing element and the tip cylinder, wherein the weather-sealing filler is configured to deform to allow the resistance sensing element to displace.

7. The apparatus of claim 1, comprising an optical sensor configured to measure a distance of displacement, and wherein the processor is configured to determine the depth of penetration based at least in part on the distance of displacement measured by the optical sensor.

8. The apparatus of claim 1, comprising an accelerometer, wherein the processor is configured to determine the depth of penetration based at least in part on an acceleration measured by the accelerometer.

9. The apparatus of claim 1, comprising a data display screen.

10. The apparatus of claim 1, comprising a wireless communication device configured to automatically determine the geographical position of the apparatus.

11. The apparatus of claim 1, comprising a wireless communication module for communicating with at least one of a wireless data network and a mobile device.

12. The apparatus of claim 1, wherein the range sensor is configured to measure distance by transmitting and receiving a beam of radiation.

13. The apparatus of claim 1, wherein the range sensor is configured to measure distance using sound waves.

14. A method for measuring snow structure and stability comprising:
    (a) measuring, at a probe while being inserted progressively deeper into a snow layer, a size of snow grains within the snow layer;
    (b) measuring a depth of penetration based on the distance measured by a range sensor; and (c) repeating steps (a)-(b) to determine a profile of snow grain size according to depth based on the measured size of snow grains and the measured depth of penetration.

15. The method of claim 14, further comprising:
determining to start a test based on at least one of a sensed resistance to penetration and input from an optical sensor; and
determining to end the test when the measured depth of penetration decreases or remains constant for a predetermined period of time.

16. The method of claim 14, further comprising averaging the measured sizes of snow grains that are within a predetermined threshold of each other.

17. The method of claim 14, wherein measuring the depth of penetration is based at least in part on a displacement measured by an optical sensor.

* * * * *